US012779027B2

(12) United States Patent
Xu et al.

(10) Patent No.: US 12,779,027 B2
(45) Date of Patent: Nov. 3, 2026

(54) C-TERMINALLY MODIFIED HUMAN PAPILLOMAVIRUS TYPE 11 L1 PROTEIN AND USE THEREOF

(71) Applicant: INSTITUTE OF BASIC MEDICAL SCIENCES, CHINESE ACADEMY OF MEDICAL SCIENCES, Beijing (CN)

(72) Inventors: Xuemei Xu, Beijing (CN); Ting Zhang, Beijing (CN); Baicheng Xia, Beijing (CN)

(73) Assignee: INSTITUTE OF BASIC MEDICAL SCIENCES, CHINESE ACADEMY OF MEDICAL SCIENCES, Beijing (CN)

( * ) Notice: Subject to any disclaimer, the term of this patent is extended or adjusted under 35 U.S.C. 154(b) by 661 days.

(21) Appl. No.: 18/254,157

(22) PCT Filed: Sep. 26, 2021

(86) PCT No.: PCT/CN2021/120517
§ 371 (c)(1),
(2) Date: May 23, 2023

(87) PCT Pub. No.: WO2022/111021
PCT Pub. Date: Jun. 2, 2022

(65) Prior Publication Data
US 2024/0000915 A1 Jan. 4, 2024

(30) Foreign Application Priority Data
Nov. 26, 2020 (CN) ........................ 202011346631.0

(51) Int. Cl.
*A61K 39/00* (2006.01)
*A61K 39/12* (2006.01)
*A61P 31/20* (2006.01)
*C07K 14/005* (2006.01)

(52) U.S. Cl.
CPC .............. *A61K 39/12* (2013.01); *A61P 31/20* (2018.01); *C07K 14/005* (2013.01); *A61K 2039/5258* (2013.01)

(58) Field of Classification Search
CPC ............ A61K 39/12; A61K 2039/5258; A61K 2039/525; A61K 2039/545; A61K 2039/70; A61K 2039/892; A61P 31/20; C07K 14/005; C07K 14/025; C12N 2710/20034; C12N 7/00; C12N 15/63; C12N 15/866; C12N 15/86; C12N 2710/14043; C12N 2710/20022; C12N 10/20023; C12N 2800/105; C12N 2800/22
See application file for complete search history.

(56) References Cited

U.S. PATENT DOCUMENTS 6,165,471 A 12/2000 Garcea et al.
7,572,882 B2 * 8/2009 Sette ...................... A61P 35/00 530/300

FOREIGN PATENT DOCUMENTS

| | | | | |
|---|---|---|---|---|
| CN | 1578787 A | | 2/2005 | |
| CN | 104418942 A | * | 3/2015 | C07K 14/005 |
| CN | 104710515 A | * | 6/2015 | A61K 39/12 |
| CN | 106831958 A | | 6/2017 | |
| EP | 0 863 982 B1 | | 1/2004 | |
| WO | 00/35479 | | 6/2000 | |

OTHER PUBLICATIONS

Zhou J, Doorbar J, Sun XY, Crawford LV, McLean CS, Frazer IH. Identification of the nuclear localization signal of human papillomavirus type 16 L1 protein. Virology. Dec. 1991;185(2):625-32. (Year: 1991).*

Chen XS, Casini G, Harrison SC, Garcea RL. Papillomavirus capsid protein expression in *Escherichia coli*: purification and assembly of HPV11 and HPV16 L1. J Mol Biol. Mar. 16, 2001;307(1):173-82. (Year: 2001).*

Rose RC, Bonnez W, Da Rin C, McCance DJ, Reichman RC. Serological differentiation of human papillomavirus types 11, 16 and 18 using recombinant virus-like particles. J Gen Virol. Sep. 1994;75 ( Pt 9):2445-9. (Year: 1994).*

Sun et al 2016. Development a scalable production process for truncated human papillomavirus type-6 L1 protein using WAVE Bioreactor and hollow fiber membrane. Appl Microbiol Biotechnol. Feb. 2016;100(3):1231-1240. (Year: 2016).*

Buck CB, Day PM, Trus BL. The papillomavirus major capsid protein L1. Virology. Oct. 2013;445(1-2):169-74. (Year: 2013).*

Joyce JG, Tung JS, Przysiecki CT, Cook JC, Lehman ED, Sands JA, Jansen KU, Keller PM. The L1 major capsid protein of human papillomavirus type 11 recombinant virus-like particles interacts with heparin and cell-surface glycosaminoglycans on human keratinocytes. J Biol Chem. Feb. 26, 1999;274(9):5810-22. (Year: 1999).*

(Continued)

*Primary Examiner* — Bennett M Celsa
*Assistant Examiner* — Samadhan Jaising Jadhao
(74) *Attorney, Agent, or Firm* — Fuller IP Law, LLC; Rodney J. Fuller

(57) ABSTRACT

The present application relates to a C-terminus modified human papillomavirus type 11 L1 protein and the use thereof. Specifically, the present application relates to a C-terminus modified human papillomavirus (HPV) type 11 L1 protein, a nucleotide encoded thereby, a vector containing the nucleotide, a cell containing the vector, a pentamer or virus-like particle composed of the HPV11 L1 protein, and a vaccine containing the pentamer or virus-like particle and a vaccine adjuvant, and the use thereof in the prevention of HPV infection and HPV infection-related diseases.

11 Claims, 4 Drawing Sheets

Specification includes a Sequence Listing.

(56) References Cited

OTHER PUBLICATIONS

Yang J, Wang YL, Si LS. Predicting the nuclear localization signals of 107 types of HPV L1 proteins by bioinformatic analysis. Genomics Proteomics Bioinformatics. Feb. 2006;4(1):34-41. (Year: 2006).*
García-Perdomo, H. A., Osorio, J. C., Fernandez, A., Zapata-Copete, J. A., & Castillo, A. (2019). The effectiveness of vaccination to prevent the papillomavirus infection: a systematic review and meta-analysis. Epidemiology & Infection, 147, e156. (Year: 2019).*

* cited by examiner

SEQUENCE LISTING

<160> NUMBER OF SEQ ID NOS: 14

<210> SEQ ID NO 1
<211> LENGTH: 501
<212> TYPE: PRT
<213> ORGANISM: Human papillomavirus type 11

<400> SEQUENCE: 1

```
Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320
```

Cys Trp Gly Asn His Leu Phe Val Thr Val Val Asp Thr Thr Arg Ser
325 330 335

Thr Asn Met Thr Leu Cys Ala Ser Val Ser Lys Ser Ala Thr Tyr Thr
340 345 350

Asn Ser Asp Tyr Lys Glu Tyr Met Arg His Val Glu Glu Phe Asp Leu
355 360 365

Gln Phe Ile Phe Gln Leu Cys Ser Ile Thr Leu Ser Ala Glu Val Met
370 375 380

Ala Tyr Ile His Thr Met Asn Pro Ser Val Leu Glu Asp Trp Asn Phe
385 390 395 400

Gly Leu Ser Pro Pro Pro Asn Gly Thr Leu Glu Asp Thr Tyr Arg Tyr
405 410 415

Val Gln Ser Gln Ala Ile Thr Cys Gln Lys Pro Thr Pro Glu Lys Glu
420 425 430

Lys Gln Asp Pro Tyr Lys Asp Met Ser Phe Trp Glu Val Asn Leu Lys
435 440 445

Glu Lys Phe Ser Ser Glu Leu Asp Gln Phe Pro Leu Gly Arg Lys Phe
450 455 460

Leu Leu Gln Ser Gly Tyr Arg Gly Arg Thr Ser Ala Arg Thr Gly Ile
465 470 475 480

Lys Arg Pro Ala Val Ser Lys Pro Ser Thr Ala Pro Lys Arg Lys Arg
485 490 495

Thr Lys Thr Lys Lys
500

<210> SEQ ID NO 2
<211> LENGTH: 501
<212> TYPE: PRT
<213> ORGANISM: Artificial Sequence
<220> FEATURE:
<223> OTHER INFORMATION: Modified HPV11 L1

<400> SEQUENCE: 2

Met Trp Arg Pro Ser Asp Ser Thr Val Tyr Val Pro Pro Pro Asn Pro
1 5 10 15

Val Ser Lys Val Val Ala Thr Asp Ala Tyr Val Lys Arg Thr Asn Ile
20 25 30

Phe Tyr His Ala Ser Ser Ser Arg Leu Leu Ala Val Gly His Pro Tyr
35 40 45

Tyr Ser Ile Lys Lys Val Asn Lys Thr Val Val Pro Lys Val Ser Gly
50 55 60

Tyr Gln Tyr Arg Val Phe Lys Val Val Leu Pro Asp Pro Asn Lys Phe
65 70 75 80

Ala Leu Pro Asp Ser Ser Leu Phe Asp Pro Thr Thr Gln Arg Leu Val
85 90 95

Trp Ala Cys Thr Gly Leu Glu Val Gly Arg Gly Gln Pro Leu Gly Val
100 105 110

Gly Val Ser Gly His Pro Leu Leu Asn Lys Tyr Asp Asp Val Glu Asn
115 120 125

Ser Gly Gly Tyr Gly Gly Asn Pro Gly Gln Asp Asn Arg Val Asn Val
130 135 140

Gly Met Asp Tyr Lys Gln Thr Gln Leu Cys Met Val Gly Cys Ala Pro
145 150 155 160

Pro Leu Gly Glu His Trp Gly Lys Gly Thr Gln Cys Ser Asn Thr Ser
165 170 175

```
Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Gly Thr Ser Ala Arg Thr Gly Ile
465                 470                 475                 480

Gly Ser Pro Ala Val Ser Lys Pro Ser Thr Ala Pro Asp Gly Ser Arg
                485                 490                 495

Thr Asp Thr Lys Lys
            500


<210> SEQ ID NO 3
<211> LENGTH: 501
<212> TYPE: PRT
<213> ORGANISM: Artificial Sequence
<220> FEATURE:
<223> OTHER INFORMATION: Modified HPV11 L1

<400> SEQUENCE: 3

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30
```

-continued

```
Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445
```

```
Glu Lys Phe Ser Ser Glu Leu Asp Gln Phe Pro Leu Gly Arg Lys Phe
    450                 455                 460

Leu Leu Gln Ser Gly Tyr Arg Gly Gly Thr Ser Ala Arg Thr Gly Ile
465                 470                 475                 480

Gly Ser Pro Ala Val Ser Lys Pro Ser Thr Ala Pro Gly Asp Ser Arg
                485                 490                 495

Thr Asp Thr Lys Lys
            500


<210> SEQ ID NO 4
<211> LENGTH: 501
<212> TYPE: PRT
<213> ORGANISM: Artificial Sequence
<220> FEATURE:
<223> OTHER INFORMATION: Modified HPV11 L1

<400> SEQUENCE: 4

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300
```

```
Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Gly Thr Ser Ala Arg Thr Gly Ile
465                 470                 475                 480

Gly Ser Pro Ala Val Ser Ser Pro Ser Thr Ala Pro Ser Gly Ser Gly
                485                 490                 495

Thr Gly Thr Lys Lys
            500


<210> SEQ ID NO 5
<211> LENGTH: 501
<212> TYPE: PRT
<213> ORGANISM: Artificial Sequence
<220> FEATURE:
<223> OTHER INFORMATION: Modified HPV11 L1

<400> SEQUENCE: 5

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160
```

```
Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Gly Thr Ser Ala Arg Thr Gly Ile
465                 470                 475                 480

Gly Ser Pro Ala Val Ser Lys Pro Ser Thr Ala Pro Ser Gly Ser Gly
                485                 490                 495

Thr Gly Thr Lys Lys
            500


<210> SEQ ID NO 6
<211> LENGTH: 501
<212> TYPE: PRT
<213> ORGANISM: Artificial Sequence
<220> FEATURE:
<223> OTHER INFORMATION: Modified HPV11 L1

<400> SEQUENCE: 6

Met Trp Arg Pro Ser Asp Ser Thr Val Tyr Val Pro Pro Pro Asn Pro
1               5                   10                  15
```

-continued

```
Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
```

```
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Asp Thr Ser Ala Arg Thr Gly Ile
465                 470                 475                 480

Gly Ser Pro Ala Val Ser Lys Pro Ser Thr Ala Pro Asp Gly Ser Arg
                485                 490                 495

Thr Asp Thr Lys Lys
            500


<210> SEQ ID NO 7
<211> LENGTH: 501
<212> TYPE: PRT
<213> ORGANISM: Artificial Sequence
<220> FEATURE:
<223> OTHER INFORMATION: Modified HPV11 L1

<400> SEQUENCE: 7

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
```

```
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Gly Thr Ser Ala Arg Thr Gly Ile
465                 470                 475                 480

Asp Ser Pro Ala Val Ser Lys Pro Ser Thr Ala Pro Asp Gly Ser Arg
                485                 490                 495

Thr Asp Thr Lys Lys
            500


<210> SEQ ID NO 8
<211> LENGTH: 1506
<212> TYPE: DNA
<213> ORGANISM: Artificial Sequence
<220> FEATURE:
<223> OTHER INFORMATION: Modified HPV11 L1

<400> SEQUENCE: 8

atgtggcgtc cctcagattc aaccgtgtac gtcccccccc ctaatcccgt gtccaaagtc      60

gtcgctaccg acgcctacgt caagaggaca aatatcttct accacgcttc atccagccgc     120

ttgttggccg tcggccaccc ctactacagc attaagaagg tcaataagac cgtcgtgccc     180

aaagtcagcg gctaccagta ccgcgtcttc aaagtggtcc tccccgaccc caataaattc     240

gccctgcccg acagctccct cttcgatcct accacccaaa ggctggtgtg ggcctgtacc     300

ggcctcgaag tgggtcgcgg ccagcccctg ggtgtcggcg tctccggcca ccccctcttg     360

aataagtacg acgacgtgga gaactccggc ggctacggcg gcaaccccgg ccaagacaac     420

cgcgtcaacg tgggcatgga ctacaagcag acacaattgt gcatggtcgg ttgcgccccc     480

cccctgggcg agcactgggg caaaggcacc cagtgcagca acacaagcgt gcagaacggc     540

gattgtcctc ccctcgagtt gatcacatcc gtcatccaag acggcgatat ggtcgacacc     600

ggtttcggcg ccatgaactt cgccgatctg cagacaaaca agagcgacgt ccctttggac     660

atctgcggca ccgtgtgtaa gtaccccgac tacctccaga tggccgccga tccctacggc     720

gaccgcctct tcttctacct caggaaagag cagatgttcg cccgccattt cttcaaccgc     780

gctggcaccg tcggcgagcc cgtccccgac gatctcctcg tgaagggcgg caacaatcgc     840
```

```
agcagcgtgg cctcctccat ctacgtgcac accccctccg gtagcctcgt cagcagcgaa    900

gcccagctgt tcaacaagcc ctactggttg cagaaagccc aaggccacaa taacggcatc    960

tgttggggca atcatctctt cgtcaccgtc gtggacacaa ccaggtccac caacatgacc   1020

ttgtgcgcca gcgtcagcaa gagcgccacc tacaccaaca gcgactacaa agagtacatg   1080

aggcacgtcg aagaattcga cctgcaattc atcttccagc tctgctcaat caccctgagc   1140

gccgaggtga tggcttacat ccataccatg aaccccagcg tcctcgaaga ttggaatttc   1200

ggtctgagcc cccccccaa cggcaccctc gaagacacct accgctacgt gcaaagccaa   1260

gctatcacat gccaaaagcc tacccccgag aaggagaagc aagaccctta caaagacatg   1320

tccttctggg aagtcaatct gaaggagaaa ttcagctccg agctggacca attccctttg   1380

ggcaggaaat tcctgctcca gtccggctac aggggccgaa ccagcgccag gaccggcatc   1440

aaaaggcccg ccgtcagcaa acctagcacc gctcctaaga ggaagaggac aaagacaaag   1500

aaataa                                                              1506


<210> SEQ ID NO 9
<211> LENGTH: 1506
<212> TYPE: DNA
<213> ORGANISM: Artificial Sequence
<220> FEATURE:
<223> OTHER INFORMATION: Modified HPV11 L1

<400> SEQUENCE: 9

atgtggcgtc cctcagattc aaccgtgtac gtcccccccc ctaatcccgt gtccaaagtc     60

gtcgctaccg acgcctacgt caagaggaca aatatcttct accacgcttc atccagccgc    120

ttgttggccg tcggccaccc ctactacagc attaagaagg tcaataagac cgtcgtgccc    180

aaagtcagcg gctaccagta ccgcgtcttc aaagtggtcc tccccgaccc caataaattc    240

gccctgcccg acagctccct cttcgatcct accacccaaa ggctggtgtg ggcctgtacc    300

ggcctcgaag tgggtcgcgg ccagcccctg ggtgtcggcg tctccggcca ccccctcttg    360

aataagtacg acgacgtgga gaactccggc ggctacggcg gcaaccccgg ccaagacaac    420

cgcgtcaacg tgggcatgga ctacaagcag acacaattgt gcatggtcgg ttgcgccccc    480

cccctgggcg agcactgggg caaaggcacc cagtgcagca acacaagcgt gcagaacggc    540

gattgtcctc ccctcgagtt gatcacatcc gtcatccaag acggcgatat ggtcgacacc    600

ggtttcggcg ccatgaactt cgccgatctg cagacaaaca agagcgacgt ccctttggac    660

atctgcggca ccgtgtgtaa gtaccccgac tacctccaga tggccgccga tccctacggc    720

gaccgcctct tcttctacct caggaaagag cagatgttcg cccgccattt cttcaaccgc    780

gctggcaccg tcggcgagcc cgtccccgac gatctcctcg tgaagggcgg caacaatcgc    840

agcagcgtgg cctcctccat ctacgtgcac accccctccg gtagcctcgt cagcagcgaa    900

gcccagctgt tcaacaagcc ctactggttg cagaaagccc aaggccacaa taacggcatc    960

tgttggggca atcatctctt cgtcaccgtc gtggacacaa ccaggtccac caacatgacc   1020

ttgtgcgcca gcgtcagcaa gagcgccacc tacaccaaca gcgactacaa agagtacatg   1080

aggcacgtcg aagaattcga cctgcaattc atcttccagc tctgctcaat caccctgagc   1140

gccgaggtga tggcttacat ccataccatg aaccccagcg tcctcgaaga ttggaatttc   1200

ggtctgagcc cccccccaa cggcaccctc gaagacacct accgctacgt gcaaagccaa   1260

gctatcacat gccaaaagcc tacccccgag aaggagaagc aagaccctta caaagacatg   1320

tccttctggg aagtcaatct gaaggagaaa ttcagctccg agctggacca attccctttg   1380
```

```
ggcaggaaat tcctgctcca gtccggctac aggggcggaa ccagcgccag gaccggcatc   1440

ggaagtcccg ccgtcagcaa acctagcacc gctcctgacg gaagcaggac agacacaaag   1500

aaataa                                                              1506
```

<210> SEQ ID NO 10
<211> LENGTH: 1506
<212> TYPE: DNA
<213> ORGANISM: Artificial Sequence
<220> FEATURE:
<223> OTHER INFORMATION: Modified HPV11 L1

<400> SEQUENCE: 10

```
atgtggcgtc cctcagattc aaccgtgtac gtcccccccc ctaatcccgt gtccaaagtc     60

gtcgctaccg acgcctacgt caagaggaca aatatcttct accacgcttc atccagccgc    120

ttgttggccg tcggccaccc ctactacagc attaagaagg tcaataagac cgtcgtgccc    180

aaagtcagcg gctaccagta ccgcgtcttc aaagtggtcc tccccgaccc caataaattc    240

gccctgcccg acagctccct cttcgatcct accacccaaa ggctggtgtg ggcctgtacc    300

ggcctcgaag tgggtcgcgg ccagcccctg ggtgtcggcg tctccggcca ccccctcttg    360

aataagtacg acgacgtgga gaactccggc ggctacggcg gcaaccccgg ccaagacaac    420

cgcgtcaacg tgggcatgga ctacaagcag acacaattgt gcatggtcgg ttgcgccccc    480

cccctgggcg agcactgggg caaaggcacc cagtgcagca acacaagcgt gcagaacggc    540

gattgtcctc ccctcgagtt gatcacatcc gtcatccaag acggcgatat ggtcgacacc    600

ggtttcggcg ccatgaactt cgccgatctg cagacaaaca agagcgacgt ccctttggac    660

atctgcggca ccgtgtgtaa gtaccccgac tacctccaga tggccgccga tccctacggc    720

gaccgcctct tcttctacct caggaaagag cagatgttcg cccgccattt cttcaaccgc    780

gctggcaccg tcggcgagcc cgtccccgac gatctcctcg tgaagggcgg caacaatcgc    840

agcagcgtgg cctcctccat ctacgtgcac acccccctccg gtagcctcgt cagcagcgaa    900

gcccagctgt tcaacaagcc ctactggttg cagaaagccc aaggccacaa taacggcatc    960

tgttggggca atcatctctt cgtcaccgtc gtggacacaa ccaggtccac caacatgacc   1020

ttgtgcgcca gcgtcagcaa gagcgccacc tacaccaaca gcgactacaa agagtacatg   1080

aggcacgtcg aagaattcga cctgcaattc atcttccagc tctgctcaat caccctgagc   1140

gccgaggtga tggcttacat ccataccatg aaccccagcg tcctcgaaga ttggaatttc   1200

ggtctgagcc ccccccccaa cggcaccctc gaagacacct accgctacgt gcaaagccaa   1260

gctatcacat gccaaaagcc tacccccgag aaggagaagc aagaccctta caaagacatg   1320

tccttctggg aagtcaatct gaaggagaaa ttcagctccg agctggacca attccctttg   1380

ggcaggaaat tcctgctcca gtccggctac aggggcggaa ccagcgccag gaccggcatc   1440

ggaagtcccg ccgtcagcaa acctagcacc gctcctggag acagcaggac agacacaaag   1500

aaataa                                                              1506
```

<210> SEQ ID NO 11
<211> LENGTH: 1506
<212> TYPE: DNA
<213> ORGANISM: Artificial Sequence
<220> FEATURE:
<223> OTHER INFORMATION: Modified HPV11 L1

<400> SEQUENCE: 11

```
atgtggcgtc cctcagattc aaccgtgtac gtcccccccc ctaatcccgt gtccaaagtc     60
gtcgctaccg acgcctacgt caagaggaca aatatcttct accacgcttc atccagccgc    120
ttgttggccg tcggccaccc ctactacagc attaagaagg tcaataagac cgtcgtgccc    180
aaagtcagcg gctaccagta ccgcgtcttc aaagtggtcc tccccgaccc caataaattc    240
gccctgcccg acagctccct cttcgatcct accacccaaa ggctggtgtg ggcctgtacc    300
ggcctcgaag tgggtcgcgg ccagcccctg ggtgtcggcg tctccggcca ccccctcttg    360
aataagtacg acgacgtgga gaactccggc ggctacggcg gcaaccccgg ccaagacaac    420
cgcgtcaacg tgggcatgga ctacaagcag acacaattgt gcatggtcgg ttgcgccccc    480
cccctgggcg agcactgggg caaaggcacc cagtgcagca acacaagcgt gcagaacggc    540
gattgtcctc ccctcgagtt gatcacatcc gtcatccaag acggcgatat ggtcgacacc    600
ggtttcggcg ccatgaactt cgccgatctg cagacaaaca agagcgacgt ccctttggac    660
atctgcggca ccgtgtgtaa gtaccccgac tacctccaga tggccgccga tccctacggc    720
gaccgcctct tcttctacct caggaaagag cagatgttcg cccgccattt cttcaaccgc    780
gctggcaccg tcggcgagcc cgtccccgac gatctcctcg tgaagggcgg caacaatcgc    840
agcagcgtgg cctcctccat ctacgtgcac accccctccg gtagcctcgt cagcagcgaa    900
gcccagctgt tcaacaagcc ctactggttg cagaaagccc aaggccacaa taacggcatc    960
tgttggggca atcatctctt cgtcaccgtc gtggacacaa ccaggtccac caacatgacc   1020
ttgtgcgcca gcgtcagcaa gagcgccacc tacaccaaca gcgactacaa agagtacatg   1080
aggcacgtcg aagaattcga cctgcaattc atcttccagc tctgctcaat caccctgagc   1140
gccgaggtga tggcttacat ccataccatg aaccccagcg tcctcgaaga ttggaatttc   1200
ggtctgagcc ccccccccaa cggcaccctc gaagacacct accgctacgt gcaaagccaa   1260
gctatcacat gccaaaagcc tacccccgag aaggagaagc aagaccctta caaagacatg   1320
tccttctggg aagtcaatct gaaggagaaa ttcagctccg agctggacca attccctttg   1380
ggcaggaaat tcctgctcca gtccggctac aggggcggaa ccagcgccag gaccggcatc   1440
ggaagtcccg ccgtcagctc acctagcacc gctcctagcg gaagcggcac aggcacaaag   1500
aaataa                                                              1506
```

```
<210> SEQ ID NO 12
<211> LENGTH: 1506
<212> TYPE: DNA
<213> ORGANISM: Artificial Sequence
<220> FEATURE:
<223> OTHER INFORMATION: Modified HPV11 L1

<400> SEQUENCE: 12
```

```
atgtggcgtc cctcagattc aaccgtgtac gtcccccccc ctaatcccgt gtccaaagtc     60
gtcgctaccg acgcctacgt caagaggaca aatatcttct accacgcttc atccagccgc    120
ttgttggccg tcggccaccc ctactacagc attaagaagg tcaataagac cgtcgtgccc    180
aaagtcagcg gctaccagta ccgcgtcttc aaagtggtcc tccccgaccc caataaattc    240
gccctgcccg acagctccct cttcgatcct accacccaaa ggctggtgtg ggcctgtacc    300
ggcctcgaag tgggtcgcgg ccagcccctg ggtgtcggcg tctccggcca ccccctcttg    360
aataagtacg acgacgtgga gaactccggc ggctacggcg gcaaccccgg ccaagacaac    420
cgcgtcaacg tgggcatgga ctacaagcag acacaattgt gcatggtcgg ttgcgccccc    480
cccctgggcg agcactgggg caaaggcacc cagtgcagca acacaagcgt gcagaacggc    540
```

```
gattgtcctc ccctcgagtt gatcacatcc gtcatccaag acggcgatat ggtcgacacc    600

ggtttcggcg ccatgaactt cgccgatctg cagacaaaca agagcgacgt cccttttggac   660

atctgcggca ccgtgtgtaa gtaccccgac tacctccaga tggccgccga tccctacggc    720

gaccgcctct tcttctacct caggaaagag cagatgttcg cccgccattt cttcaaccgc    780

gctggcaccg tcggcgagcc cgtccccgac gatctcctcg tgaagggcgg caacaatcgc    840

agcagcgtgg cctcctccat ctacgtgcac accccctccg gtagcctcgt cagcagcgaa    900

gcccagctgt tcaacaagcc ctactggttg cagaaagccc aaggccacaa taacggcatc    960

tgttggggca atcatctctt cgtcaccgtc gtggacacaa ccaggtccac caacatgacc   1020

ttgtgcgcca gcgtcagcaa gagcgccacc tacaccaaca gcgactacaa agagtacatg   1080

aggcacgtcg aagaattcga cctgcaattc atcttccagc tctgctcaat caccctgagc   1140

gccgaggtga tggcttacat ccataccatg aaccccagcg tcctcgaaga ttggaatttc   1200

ggtctgagcc cccccccaa cggcaccctc gaagacacct accgctacgt gcaaagccaa    1260

gctatcacat gccaaaagcc taccccgag aaggagaagc aagaccctta caaagacatg    1320

tccttctggg aagtcaatct gaaggagaaa ttcagctccg agctggacca attccctttg   1380

ggcaggaaat tcctgctcca gtccggctac aggggcggaa ccagcgccag gaccggcatc   1440

ggaagtcccg ccgtcagcaa acctagcacc gctcctagcg gaagcggcac aggcacaaag   1500

aaataa                                                               1506
```

```
<210> SEQ ID NO 13
<211> LENGTH: 1506
<212> TYPE: DNA
<213> ORGANISM: Artificial Sequence
<220> FEATURE:
<223> OTHER INFORMATION: Modified HPV11 L1

<400> SEQUENCE: 13

atgtggcgtc cctcagattc aaccgtgtac gtcccccccc ctaatcccgt gtccaaagtc     60

gtcgctaccg acgcctacgt caagaggaca aatatcttct accacgcttc atccagccgc    120

ttgttggccg tcggccaccc ctactacagc attaagaagg tcaataagac cgtcgtgccc    180

aaagtcagcg gctaccagta ccgcgtcttc aaagtggtcc tccccgaccc caataaattc    240

gccctgcccg acagctccct cttcgatcct accacccaaa ggctggtgtg ggcctgtacc    300

ggcctcgaag tgggtcgcgg ccagcccctg ggtgtcggcg tctccggcca ccccctcttg    360

aataagtacg acgacgtgga gaactccggc ggctacggcg gcaaccccgg ccaagacaac    420

cgcgtcaacg tgggcatgga ctacaagcag acacaattgt gcatggtcgg ttgcgccccc    480

cccctgggcg agcactgggg caaaggcacc cagtgcagca acacaagcgt gcagaacggc    540

gattgtcctc ccctcgagtt gatcacatcc gtcatccaag acggcgatat ggtcgacacc    600

ggtttcggcg ccatgaactt cgccgatctg cagacaaaca agagcgacgt ccctttggac    660

atctgcggca ccgtgtgtaa gtaccccgac tacctccaga tggccgccga tccctacggc    720

gaccgcctct tcttctacct caggaaagag cagatgttcg cccgccattt cttcaaccgc    780

gctggcaccg tcggcgagcc cgtccccgac gatctcctcg tgaagggcgg caacaatcgc    840

agcagcgtgg cctcctccat ctacgtgcac accccctccg gtagcctcgt cagcagcgaa    900

gcccagctgt tcaacaagcc ctactggttg cagaaagccc aaggccacaa taacggcatc    960

tgttggggca atcatctctt cgtcaccgtc gtggacacaa ccaggtccac caacatgacc   1020
```

ttgtgcgcca gcgtcagcaa gagcgccacc tacaccaaca gcgactacaa agagtacatg 1080
aggcacgtcg aagaattcga cctgcaattc atcttccagc tctgctcaat caccctgagc 1140
gccgaggtga tggcttacat ccataccatg aaccccagcg tcctcgaaga ttggaatttc 1200
ggtctgagcc cccccccaa cggcaccctc gaagacacct accgctacgt gcaaagccaa 1260
gctatcacat gccaaaagcc tacccccgag aaggagaagc aagacccctta caaagacatg 1320 tccttctggg aagtcaatct gaaggagaaa ttcagctccg agctggacca attccctttg 1380
ggcaggaaat tcctgctcca gtccggctac aggggcgaca ccagcgccag gaccggcatc 1440
ggaagtcccg ccgtcagcaa acctagcacc gctcctgacg gaagcaggac agacacaaag 1500
aaataa 1506

<210> SEQ ID NO 14
<211> LENGTH: 1506
<212> TYPE: DNA
<213> ORGANISM: Artificial Sequence
<220> FEATURE:
<223> OTHER INFORMATION: Modified HPV11 L1

<400> SEQUENCE: 14
atgtggcgtc cctcagattc aaccgtgtac gtcccccccc ctaatcccgt gtccaaagtc 60
gtcgctaccg acgcctacgt caagaggaca aatatcttct accacgcttc atccagccgc 120
ttgttggccg tcggccaccc ctactacagc attaagaagg tcaataagac cgtcgtgccc 180
aaagtcagcg gctaccagta ccgcgtcttc aaagtggtcc tccccgaccc caataaattc 240
gccctgcccg acagctccct cttcgatcct accacccaaa ggctggtgtg ggcctgtacc 300
ggcctcgaag tgggtcgcgg ccagcccctg ggtgtcggcg tctccggcca ccccctcttg 360
aataagtacg acgacgtgga gaactccggc ggctacggcg gcaaccccgg ccaagacaac 420
cgcgtcaacg tgggcatgga ctacaagcag acacaattgt gcatggtcgg ttgcgccccc 480
cccctgggcg agcactgggg caaaggcacc cagtgcagca acacaagcgt gcagaacggc 540
gattgtcctc ccctcgagtt gatcacatcc gtcatccaag acggcgatat ggtcgacacc 600
ggtttcggcg ccatgaactt cgccgatctg cagacaaaca agagcgacgt cccctttggac 660 atctgcggca ccgtgtgtaa gtaccccgac tacctccaga tggccgccga tccctacggc 720
gaccgcctct tcttctacct caggaaagag cagatgttcg cccgccattt cttcaaccgc 780
gctggcaccg tcggcgagcc cgtccccgac gatctcctcg tgaagggcgg caacaatcgc 840
agcagcgtgg cctcctccat ctacgtgcac accccctccg gtagcctcgt cagcagcgaa 900
gcccagctgt tcaacaagcc ctactggttg cagaaagccc aaggccacaa taacggcatc 960
tgttggggca atcatctctt cgtcaccgtc gtggacacaa ccaggtccac caacatgacc 1020
ttgtgcgcca gcgtcagcaa gagcgccacc tacaccaaca gcgactacaa agagtacatg 1080
aggcacgtcg aagaattcga cctgcaattc atcttccagc tctgctcaat caccctgagc 1140
gccgaggtga tggcttacat ccataccatg aaccccagcg tcctcgaaga ttggaatttc 1200
ggtctgagcc cccccccaa cggcaccctc gaagacacct accgctacgt gcaaagccaa 1260
gctatcacat gccaaaagcc tacccccgag aaggagaagc aagacccctta caaagacatg 1320 tccttctggg aagtcaatct gaaggagaaa ttcagctccg agctggacca attccctttg 1380

-continued

```
ggcaggaaat tcctgctcca gtccggctac aggggcggaa ccagcgccag gaccggcatc   1440

gacagtcccg ccgtcagcaa acctagcacc gctcctgacg gaagcaggac agacacaaag   1500

aaataa                                                              1506
```

C-TERMINALLY MODIFIED HUMAN PAPILLOMAVIRUS TYPE 11 L1 PROTEIN AND USE THEREOF

CROSS REFERENCE TO RELATED APPLICATIONS

The present application is the U.S. National Stage of International Application No. PCT/CN2021/120517, filed on Sep. 26, 2021, which claims the priority of Chinese Patent Application No. 202011346631.0, filed on Nov. 26, 2020, the contents of each of which are incorporated herein by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 44,258 byte ASCII (text) file named “Seq_List” created on Sep. 26, 2021.

FIELD OF THE INVENTION

The present application relates to the field of biotechnology. Specifically, the present application relates to a modified human papillomavirus protein, and a pentamer or a virus-like particle formed thereby, as well as use of the human papillomavirus protein, the pentamer or the human papillomavirus virus-like particle in the preparation of a vaccine for the prevention of papillomavirus infection and infection-induced diseases.

BACKGROUND OF THE INVENTION

Human papillomavirus (HPV) is a class of non-enveloped small DNA viruses that infect epithelial tissue. The viral genome is a double-stranded closed circular DNA of about 7.2-7.9 kb in size, with 8 open reading frames encoding a total of 6 early stage genes, E1, E2, E4, E5, E6 and E7, and a total of 2 late stage genes, L1 and L2, respectively. In addition, the genome also contains a long regulatory region. The viral particle has a diameter of about 45-44 nm. The shell is a regular icosahedron of T=7 composed of 72 L1 pentamers and 72 L2 proteins.

At present, more than 200 types of HPV have been identified, among which more than 40 types mainly infect the perianal, urogenital and oropharyngeal mucous membrane and adjacent skin. According to the nature of infection-induced lesions, they are classified into carcinogenic types that induce malignant tumors (HPV16, -18, -31, -33, -45, -52, -58, etc.) and low-risk types that induce verrucous hyperplasia (HPV6, -11, etc.). At present, there are about 20 types of carcinogenic HPV, among which 12 common carcinogenic types are high-risk types. Molecular epidemiological studies have found that persistent infection with carcinogenic HPV can induce about 100% of cervical cancer, 88% of anal cancer, 70% of vaginal cancer, 50% of penile cancer, 43% of vulva cancer, and 72% of head and neck cancer. At present, 12 types of low-risk HPV have been identified, namely HPV6, -7, -11, -13, -32, -40, -42, -43, -44, -54, -74 and -91. Among them, HPV6 and HPV11 types are the main prevalent types responsible for perianal, genital and pharyngeal mucosal warts worldwide. Analysis of HPV in a total of 10,757 condyloma acuminatum (CA) patients, from 67 literatures published in China during January 1990 to December 2013, found that the positive rate of HPV infection in CA patients was 86.7% (9328). The positive rate was 81.2% (3671/4623) for HPV6 and/or HPV11, 43.8% (2445/6134) for HPV6, 38.3% (2155/6134) for HPV11, and 21.7% (870/3781) for HPV16, HPV18 and/or HPV11. Analysis of HPV in 261 patients with genital warts (GW) diagnosed by biopsy histology in Colombia area, including 155 females and 106 males, showed that the detection rate of HPV was 87.7% in female and 90.6% in male GW patients. Among them, the detection rate of HPV6 was the highest, reaching 59.7% (155.8/261), 62% in females and 56% in males, respectively. The detection rate of HPV11 was the second highest, which was 29.8% (77.8/261). The detection rate of HPV16 ranked third, which was 16%. The total positive rate of HPV6 and HPV11 infection was 80.3%.

The L1 protein can be assembled into VLP after in vitro expression. The expression systems are mainly yeast expression systems, insect cell expression systems, *E. coli* expression systems, etc. The advantages of producing L1VLP vaccines using insect cell expression systems are high expression levels of soluble protein, easy cell disruption, and absence of endotoxin. The three L1VLP vaccines currently on the market are the Gardasil™ tetravalent vaccine (HPV16/18/6/11 L1VLP, aluminum phosphate sulfate adjuvant) and the Gardasil-9™ nine-valent vaccine (HPV16/18/6/11/31/33/45/52/58 L1VLP, aluminium phosphate sulfate adjuvant) produced by Merck using yeast expression systems, and the Cervarix™ bivalent vaccine (HPV16/18 L1VLP, AS04 adjuvant) produced by GSK using insect cell expression systems.

Clinical studies found that the titer of HPV16 and HPV18-specific neutralizing antibodies, Th cell response and memory B cell number induced by a relatively low dose of 16L1VLP (20 μg/dose) and the same dose of 18L1VLP (20 μg/dose) of Cervarix™ were higher than those induced by Gardasil™ (40 μg of 16L1VLP and 20 μg of 18L1VLP in a single dose of Gardasil™).

Increasing the expression level of HPV L1VLP in insect cells can significantly improve the purification yield of L1VLP and reduce the production cost of the vaccine. In prokaryotic expression systems, L1 of HPV16, -18, -31, -33, -45, -52, -58, -6, and -11 types was modified by N-terminus truncation, and it was found that the number of amino acids truncated at N-terminus that could upregulate the L1 expression level varies from type to type; and was irregular. In insect expression systems, BPV1 L1 was modified by C-terminus truncation, and it was found that the assembly efficiency of truncated BPV L1 increased by 3 folds. Although the VLP of HPV58 truncated L1 has been reported, the effect of C-terminus truncation on protein expression has not been reported. When using yeast expression systems, type 11 L1VLP was produced using codon-optimized full-length gene.

It has been found in the present application that C-terminus modification of L1 can significantly increase the expression level and yield of 11L1VLP, and the obtained HPV11 L1VLP can induce high titers of type-specific neutralizing antibodies.

SUMMARY OF THE INVENTION

The present application provides a novel C-terminus modified HPV11 L1 protein, a pentamer or a virus-like particle composed thereof, and a vaccine containing the pentamer or virus-like particle, and studies use of the vaccine in the prevention of HPV infection and infection-related diseases.

The inventor has unexpectedly found that appropriate substitution of C-terminus basic amino acids of HPV11 L1 protein can increase the expression amount of HPV11 L1 protein in insect cell expression systems. The truncated protein can be assembled into VLP and can induce a protective immune response against HPV11.

Thus, according to some embodiments of the present application, the present application relates to a HPV11 L1 protein, wherein one or more of the 31 basic amino acids at C-terminus substituted with polar uncharged amino acids, non-polar amino acids and/or acidic amino acids, compared with wild-type HPV11 L1 protein (e.g., the amino acid sequence corresponding to the sequence P04012.1, corresponding to SEQ ID No. 1, in NATIONAL CENTER FOR BIOTECHNOLOGY INFORMATION database).

Specifically, the present application provides a C-terminus modified HPV11 L1 protein, wherein one or more arginine (R) and/or lysine (K) within the 31 C-terminus amino acids of the modified HPV11 L1 protein are substituted with polar uncharged amino acids, non-polar amino acids and/or acidic amino acids, compared with wild-type HPV11 L1 protein. Preferably, the polar uncharged amino acid is selected from the group consisting of glycine (G), serine (S) and threonine (T), the non-polar amino acid is selected from the group consisting of alanine (A) and valine (V), and the acidic amino acid is aspartate (D) or glutamate (E).

In particular embodiments, the C-terminus modified HPV11 L1 protein of the present application is modified on the basis of the sequence as shown in SEQ ID No. 1 (the amino acid sequence corresponding to the sequence P04012.1 in NATIONAL CENTER FOR BIOTECHNOLOGY INFORMATION database); particularly preferably, the C-terminus modified HPV11 L1 protein is selected from the group consisting of 11L1CS1, 11L1CS2, 11L1CS3, 11L1CS4, 11L1CS5 and 11L1CS6, the amino acid sequences of which are as shown in SEQ ID No. 2, SEQ ID No. 3, SEQ ID No. 4, SEQ ID No. 5, SEQ ID No. 6 and SEQ ID No. 7.

The wild-type HPV11 L1 protein can also be, but not limited to, L1 proteins from HPV11 variant strains in NATIONAL CENTER FOR BIOTECHNOLOGY INFORMATION database, and C-terminus modified L1 proteins corresponding to those variant strains, characterized by that the 31 amino acids at C-terminus are modified in the same way as that for the above-mentioned C-terminus modified HPV11 L1 protein, such as evaluated by sequence comparison.

According to some embodiments of the present application, the present application relates to a polynucleotide encoding the C-terminus modified HPV11 L1 protein of the present application. Preferably, the polynucleotide is optimized using codons of commonly used expression systems, such as *E. coli* expression systems, yeast expression systems, insect cell expression systems, etc. Preferably, the polynucleotide is optimized using insect cell codons.

According to some embodiments of the present application, the present application relates to a vector containing the above-mentioned polynucleotide. Preferably, the vector is selected from the group consisting of plasmid, recombinant Bacmid and recombinant baculovirus.

According to some embodiments of the present application, the present application relates to a cell comprising the above-mentioned vector. Preferably, the cell is an *E. coli* cell, a yeast cell or an insect cell, and particularly preferably, the cell is an insect cell.

According to some embodiments of the present application, the present application relates to a HPV11 L1 multimer or a virus-like particle, the multimer (e.g., pentamer) or virus-like particle contains the above-mentioned C-terminus modified HPV11 L1 protein or is composed of the same.

According to some embodiments of the present application, the present application relates to a vaccine for the prevention of HPV infection or HPV infection-related diseases comprising the above-mentioned HPV11 L1 multimer or virus-like particle, wherein the content of the HPV11 L1 virus-like particle is an effective amount that can induce a protective immune response. Preferably, the vaccine can also comprise at least one selected from other mucosa-tropic and/or skin-tropic HPV pentamer or virus-like particle, the content of which is an effective amount that can induce a protective immune response, respectively. The above-mentioned vaccine usually also comprises an excipient or carrier for vaccines.

Preferably, the vaccine contains the above-mentioned HPV11 L1 multimer or virus-like particle, as well as at least one selected from the group consisting of HPV2, -5, -6, -7, -8, -16, -18, -26, -27, -28, -29, -30, -31, -32, -33, -34, -35, -38, -39, -40, -43, -44, -45, -51, -52, -53, -56, -57, -58, -59, -61, -66, -67, -68, -69, -70, -73, -74, -77, -81, -82, -83, -85, -91 L1 virus-like particles, the content of which is an effective amount that can induce a protective immune response, respectively.

Further preferably, the vaccine contains the above-mentioned HPV11 L1 multimer or virus-like particle, as well as HPV6, -16, -18, -26, -31, -33, -35, -39, -45, -51, -52, -56, -58, -59, -68 and -73 L1 virus-like particles, the content of which is an effective amount that can induce a protective immune response, respectively.

Further preferably, the vaccine contains the above-mentioned HPV11 L1 multimer or virus-like particle, as well as HPV6, -16, -18, -31, -33, -35, -39, -45, -52 and -58 L1 virus-like particles, the content of which is an effective amount that can induce a protective immune response, respectively.

Further preferably, the vaccine contains the above-mentioned HPV11 L1 multimer or virus-like particle, as well as HPV6, -16, -18, -52 and -58 L1 virus-like particles, the content of which is an effective amount that can induce a protective immune response, respectively.

Further preferably, the vaccine contains the above-mentioned HPV11 L1 multimer or virus-like particle, as well as HPV16, -18 and -58 L1 virus-like particles, the content of which is an effective amount that can induce a protective immune response, respectively.

Particularly preferably, the vaccine contains the above-mentioned HPV11 L1 multimer or virus-like particle, as well as HPV6 virus-like particle, the content of which is an effective amount that can induce a protective immune response, respectively.

According to some embodiments of the present application, the present application relates to a novel vaccine comprising the above-mentioned HPV11 L1 multimer or virus-like particle as well as an adjuvant, which can further enhance the immune response. Preferably, the adjuvant used is a human vaccine adjuvant.

According to some embodiments of the present application, the present application relates to use of the above-mentioned vaccine in the prevention of HPV infection or HPV infection-related diseases.

Description and Explanation of Relevant Terms

According to the present application, the term "insect cell expression system" includes insect cell, recombinant baculovirus, recombinant Bacmid and expression vector. Among them, the insect cell is derived from a commercially available cell, the examples of which are listed here but not limited to: Sf9, Sf21, High Five.

According to the present application, examples of the term "wild-type HPV11 L1 protein" include, but are not limited to, L1 protein corresponding to the sequence No. P04012.1 in NATIONAL CENTER FOR BIOTECHNOLOGY INFORMATION database.

According to the present application, the term "excipient or carrier" refers to that selected from one or more of the following, including but not limited to, pH adjuster, surfactant and ionic strength enhancer. For example, the pH adjuster is for example but not limited to phosphate buffer. The surfactant includes cationic, anionic or nonionic surfactant, and is for example but not limited to polysorbate 80. The ionic strength enhancer is for example but not limited to sodium chloride.

According to the present application, the term "adjuvant" refers to an adjuvant that can be applied clinically to the human body, including various adjuvants that have been approved and may be approved in the future.

According to the present application, the vaccine of the present application can be in a patient-acceptable form, including but not limited to oral administration or injection, preferably injection.

According to the present application, the vaccine of the present application is preferably used in a unit dosage form, wherein the dose of the C-terminus modified HPV11 L1 protein virus-like particle in the unit dosage form is 5 μg-80 μg, preferably 20 μg-40 μg.

DESCRIPTION OF THE DRAWINGS

FIG. 2A represents wild-type HPV11L1, FIG. 2B represents 11L1CS1, FIG. 2C represents 11L1CS3, FIG. 2D represents 11L1CS4, and FIG. 2E represents 11L1CS5.

FIGS. 3A, 3B and 3C represent wild-type HPV11L1, 11L1CS4 and 11L1CS5, respectively.

DETAILED DESCRIPTION OF THE INVENTION

Figure 1:
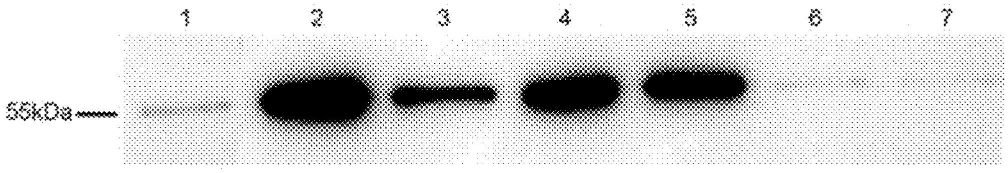
FIG. 1 shows the expression identification of the C-terminus modified HPV11 L1 in Example 4 of the present application in insect cells. The results show that all six types of C-terminus modified HPV11 L1 can be expressed in insect cells. Lanes 1 to 7 represent wild-type HPV11L1, 11L1CS1, 11L1CS3, 11L1CS4, 11L1CS5, 11L1CS6 and 11L1CS2, respectively.
Figure 2A:
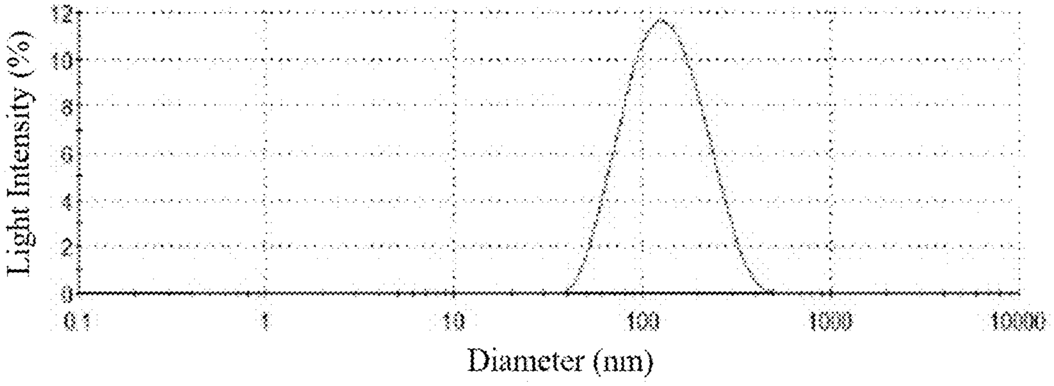
FIGS. 2A to 2E show the dynamic light scattering analysis results of wild-type HPV11L1, 11L1CS1, 11L1CS3, 11L1CS4 and 11L1CS5 mutant proteins obtained after purification in Example 6 of the present application. The results show that the hydraulic diameters of the virus-like particles formed by wild-type HPV11L1, 11L1CS1, 11L1CS3, 11L1CS4 and 11L1CS5 recombinant proteins are 117 nm, 143 nm, 95.2 nm, 121 nm and 119 nm, respectively, and the percentages of particle assembly are all 100%.
Figure 2B:
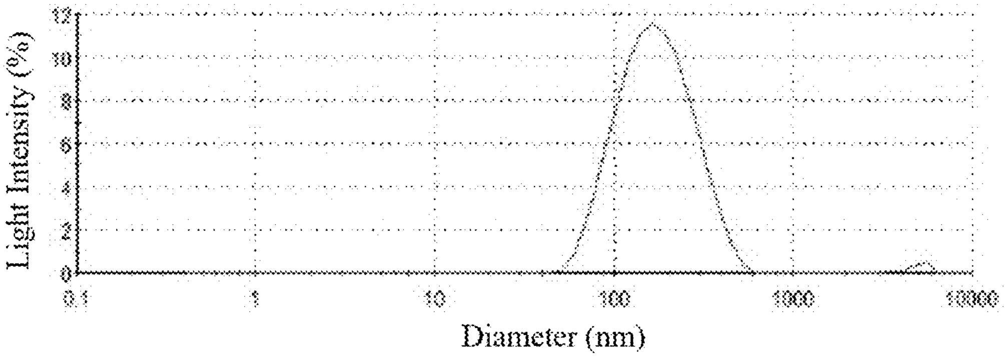
Figure 2C:
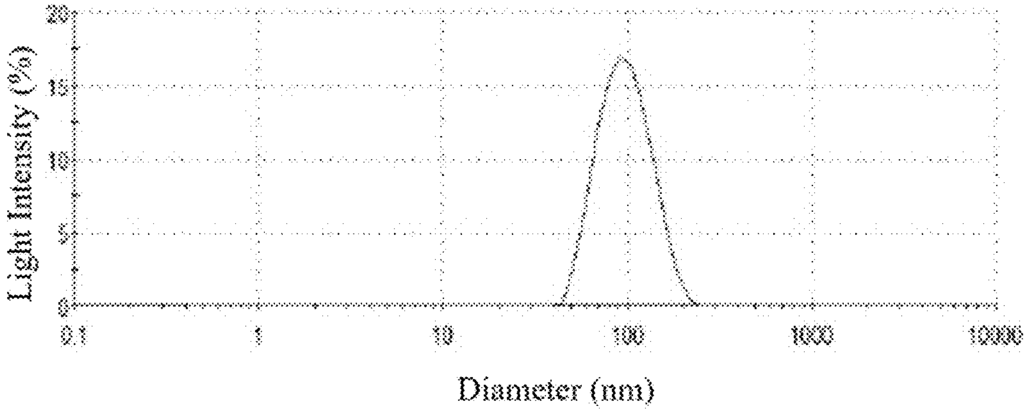
Figure 2D:
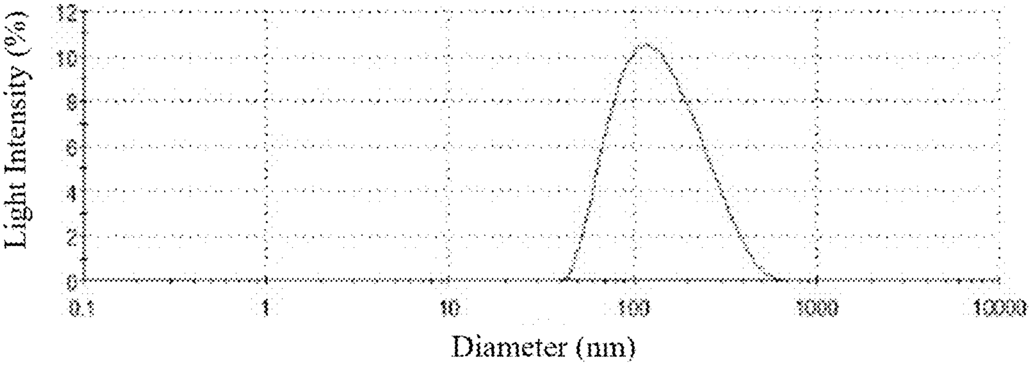
Figure 2E:
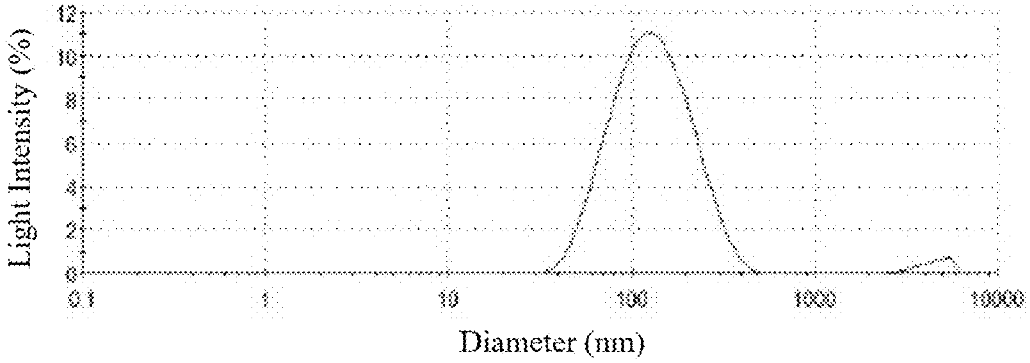

The present application will be further illustrated by the non-limiting examples below. It is well known to those skilled in the art that many modifications can be made to the present application without departing from the spirit of the present application, and such modifications also fall within the scope of the present application. The following embodiments are only used to illustrate the present application and should not be regarded as limiting the scope of the present application, as the embodiments are necessarily diverse. The terms used in the present specification are intended only to describe particular embodiments but not as limitations. The scope of the present application has been defined in the appended claims.

Unless otherwise specified, all the technical and scientific terms used in the present specification have the same meaning as those generally understood by those skilled in the technical field to which the present application relates. Preferred methods and materials of the present application are described below, but any method and material similar or equivalent to the methods and materials described in the present specification can be used to implement or test the present application. Unless otherwise specified, the following experimental methods are conventional methods or methods described in product specifications. Unless otherwise specified, the experimental materials used are easily available from commercial companies. All published literatures referred to in the present specification are incorporated here by reference to reveal and illustrate the methods and/or materials in the published literatures.

Example 1: Synthesis of C-Terminus Modified HPV11L1 Gene and Construction of Expression Vectors The amino acid sequence of wild-type HPV11L1 was the sequence as shown in SEQ ID No. 1, and its corresponding insect cell codon-optimized full-length gene (as shown in SEQ ID No. 8) was whole-gene synthesized by Shanghai Sangon Biotech Co., Ltd.

The C-terminus modified HPV11L1 genes were modified on the basis of the gene as shown in SEQ ID No. 8, and were synthesized by Shanghai Sangon Biotech Co., Ltd. The details were as follows:

1) 11L1CS1 gene: In HPV11L1 as shown in SEQ ID No. 1, the arginine (R) at position 473 was mutated to glycine (G), the lysine (K) at position 481 was mutated to glycine (G), the arginine (R) at position 482 was mutated to serine (S), the lysine (K) at position 493 was mutated to aspartate (D), the arginine (R) at position 494 was mutated to glycine (G), the lysine (K) at position 495 was mutated to serine (S), and the lysine (K) at position 498 was mutated to aspartate (D). Its amino acid sequence was as shown in SEQ ID No. 2, and the corresponding nucleotide sequence was as shown in SEQ ID No. 9;
2) 11L1CS2 gene: In HPV11L1 as shown in SEQ ID No. 1, the arginine (R) at position 473 was mutated to glycine (G), the lysine (K) at position 481 was mutated to glycine (G), the arginine (R) at position 482 was mutated to serine (S), the lysine (K) at position 493 was mutated to glycine (G), the arginine (R) at position 494 was mutated to aspartate (D), the lysine (K) at position 495 was mutated to serine (S), and the lysine (K) at position 498 was mutated to aspartate (D). Its amino acid sequence was as shown in SEQ ID No. 3, and the corresponding nucleotide sequence was as shown in SEQ ID No. 10;

3) 11L1CS3 gene: In HPV11L1 as shown in SEQ ID No. 1, the arginine (R) at position 473 was mutated to glycine (G), the lysine (K) at position 481 was mutated to glycine (G), the arginine (R) at position 482 was mutated to serine (S), the lysine (K) at position 487 was mutated to serine (S), the lysine (K) at position 493 was mutated to serine (S), the arginine (R) at position 494 was mutated to glycine (G), the lysine (K) at position 495 was mutated to serine (S), the arginine (R) at position 496 was mutated to glycine (G), and the lysine (K) at position 498 was mutated to glycine (G). Its amino acid sequence was as shown in SEQ ID No. 4, and the corresponding nucleotide sequence was as shown in SEQ ID No. 11;

4) 11L1CS4 gene: In HPV11L1 as shown in SEQ ID No. 1, the arginine (R) at position 473 was mutated to glycine (G), the lysine (K) at position 481 was mutated to glycine (G), the arginine (R) at position 482 was mutated to serine (S), the lysine (K) at position 493 was mutated to serine (S), the arginine (R) at position 494 was mutated to glycine (G), the lysine (K) at position 495 was mutated to serine (S), the arginine (R) at position 496 was mutated to glycine (G), and the lysine (K) at position 498 was mutated to glycine (G). Its amino acid sequence was as shown in SEQ ID No. 5, and the corresponding nucleotide sequence was as shown in SEQ ID No. 12;

5) 11L1CS5 gene: In HPV11L1 as shown in SEQ ID No. 1, the arginine (R) at position 473 was mutated to aspartate (D), the lysine (K) at position 481 was mutated to glycine (G), the arginine (R) at position 482 was mutated to serine (S), the lysine (K) at position 493 was mutated to aspartate (D), the arginine (R) at position 494 was mutated to glycine (G), the lysine (K) at position 495 was mutated to serine (S), and the lysine (K) at position 498 was mutated to aspartate (D). Its amino acid sequence was as shown in SEQ ID No. 6, and the corresponding nucleotide sequence was as shown in SEQ ID No. 13;

6) 11L1CS6 gene: In HPV11L1 as shown in SEQ ID No. 1, the arginine (R) at position 473 was mutated to glycine (G), the lysine (K) at position 481 was mutated to aspartate (D), the arginine (R) at position 482 was mutated to serine (S), the lysine (K) at position 493 was mutated to aspartate (D), the arginine (R) at position 494 was mutated to glycine (G), the lysine (K) at position 495 was mutated to serine (S), and the lysine (K) at position 498 was mutated to aspartate (D). Its amino acid sequence was as shown in SEQ ID No. 7, and the corresponding nucleotide sequence was as shown in SEQ ID No. 14.

The EcoRI/XbaI restriction sites were used to digest the above-mentioned PCR-amplified genes respectively, which were inserted into the commercial expression vector pFastBac1™ (produced by Invitrogen) respectively to obtain recombinant expression vectors comprising the C-terminus modified HPV11L1 genes, pFastBac1-11L1CS1™, pFastBac1-11LICS2™, pFastBac1-11L1CS3™, pFastBac1-11L1CS4™, pFastBac1-11L1CS5™ and pFastBac1-11L1CS6™. The above-mentioned methods of enzyme digestion, ligation and construction of clones were all well known, for example, the patent CN 101293918 B.

Example 2: Recombinant Bacmid and Recombinant Baculovirus Constructs of the C-Terminus Modified HPV11L1 Gene The recombinant expression vectors of the C-terminus modified HPV11L1 gene, pFastBac1-11L1CS1, pFastBac1-11L1CS2, pFastBac1-11L1CS3, pFastBac1-11L1CS4, pFastBac1-11L1CS5 and pFastBac1-11L1CS6, were used to transform *E. coli* DH10Bac competent cells respectively. Screening was performed to obtain recombinant Bacmids, which were then used to transfect Sf9 insect cells to amplify recombinant baculoviruses within Sf9. Methods of recombinant Bacmid screening and recombinant baculovirus amplification were all well known, for example, the patent CN 101148661 B.

Example 3: Expression of C-Terminus Modified HPV11L1 Gene in Sf9 Cells

Sf9 cells were inoculated with the recombinant baculovirus of optimized wild-type HPV11L1 gene and the 6 C-terminus modified HPV11L1 genes to express the C-terminus modified HPV11L1 proteins. After incubation at 27° C. for about 88 h, the fermentation broth was collected and centrifuged at 3,000 rpm for 15 min. The supernatant was discarded, and the cells were washed with PBS for use in expression, identification and purification. Methods of infection and expression were publicly available, for example, the patent CN 101148661 B.

Example 4: Expression and Identification of C-Terminus Modified HPV11L1

$1\times10^6$ cells expressing the different C-terminus modified HPV11L1 described in Example 3 respectively were collected and resuspended in 200 μl PBS solution. 50 μl of 6× loading buffer was added and the samples were denatured at 75° C. for 8 minutes. 10 μl of sample was used for SDS-PAGE electrophoresis and Western blot identification, respectively. The results were as shown in FIG. 1. All 6 C-terminus modified HPV11L1 proteins could be expressed in insect cells, with a size of about 55 kDa. Methods of SDS-PAGE electrophoresis and Western blot identification were publicly available, for example, the patent CN 101148661 B.

Example 5: Comparison of Expression Amounts Between C-Terminus Modified

HPV11L1 proteins and wild-type HPV11L1 protein $1\times10^6$ cells expressing the C-terminus modified HPV11L1 proteins and wild-type HPV11L1 described in Example 3 respectively were collected and resuspended in 200 μl PBS solution. The cells were sonicated by ultrasonic disruption (Ningbo Scientz Ultrasonic Cell Disruptor, 2 #probe, 100 W, ultrasound 5 s, interval 7 s, total period 3 min) and centrifuged at a high speed of 12,000 rpm for 10 minutes. The lysed supernatant was collected and the L1 content in the supernatant was detected by sandwich ELISA, which was well known, for example, the patent CN104513826A.

Microtiter plates were coated with HPV11L1 monoclonal antibodies prepared by the inventor at 80 ng/well by overnight incubation at 4° C. The plate was blocked with 5% BSA-PBST at room temperature for 2 h and washed 3 times with PBST. The lysed supernatant was subjected to 2-fold serial dilution with PBS. The HPV11L1 VLP standard was also subjected to serial dilution from a concentration of 2 μg/ml to 0.0625 μg/ml. The diluted samples were added to the plate respectively at 100 μl per well and incubated at 37° C. for 1 h. The plate was washed 3 times with PBST, and 1:3000 diluted HPV6L1 rabbit polyclonal antibody was added at 100 μl per well and incubated at 37° C. for 1 h. The plate was washed 3 times with PBST, and 1:3000 diluted HRP-labeled goat anti-mouse IgG (1:3000 dilution, ZSGB-Bio Corporation) was added and incubated at 37° C. for 45 minutes. The plate was washed 5 times with PBST, and 100 μl of OPD substrate (Sigma) was added to each well for development at 37° C. for 5 minutes. The reaction was stopped with 50 μl of 2 M sulfuric acid, and the absorbance at 490 nm was determined. The concentrations of C-terminus modified HPV11L1 proteins and wild-type HPV11L1 protein in the lysed supernatant were calculated according to the standard curve.

The results were as shown in Table 1. The expression amounts of C-terminus modified 11L1CS1, 11L1CS3, 11L1CS4 and 11L1CS5 of the present application were higher than that of wild-type HPV11L1 protein, while the expression amounts of 11L1CS2 and 11L1CS6 were comparable to that of wild-type 11L1.

TABLE 1

Analysis of expression amounts of HPV11L1 proteins

| Protein | Expression amount (mg/L) | | | |
|---|---|---|---|---|
| name | Batch 1 | Batch 2 | Batch 3 | Average |
| HPV11L1 | 24 | 29 | 21 | 24.67 |
| 11L1CS1 | 166 | 170 | 173 | 169.7 |
| 11L1CS2 | 20 | 25 | 27 | 24 |
| 11L1CS3 | 59 | 51 | 53 | 54.33 |
| 11L1CS4 | 141 | 153 | 156 | 150 |
| 11L1CS5 | 139 | 128 | 133 | 133.3 |
| 11L1CS6 | 20 | 18 | 26 | 21.33 |

Example 6: Purification and Dynamic Light Scattering Particle Size Analysis of C-Terminus Modified HPV11L1 Proteins 50 ml of cell fermentation broth of wild-type HPV11L1 or C-terminus modified HPV11L1 was collected and the cells were resuspended with 10 ml of PBS. PMSF was added to a final concentration of 1 mg/ml. The cells were ultrasonically disrupted (Ningbo Scientz Ultrasonic Cell Disruptor, 6 #probe, 100 W, ultrasound 5 s, interval 7 s, total period 5 min) and the disrupted supernatant was collected for purification. The purification steps were carried out at room temperature. 4% β-mercaptoethanol (w/w) was added to the lysate to depolymerize VLP. Then the samples were filtered with 0.22 μm filters, followed by successive purification with DMAE anion exchange chromatography (20 mM Tris, 180 mM NaCl, 4% β-ME, elution at pH 7.9), TMAE anion exchange chromatography (20 mM Tris, 180 mM NaCl, 4% β-ME, elution at pH 7.9) and hydroxyapatite chromatography (100 mM NaH.sub.2PO.sub.4, 30 mM NaCl, 4% β-ME, elution at pH 6.0). The purified product was concentrated using Planova™ ultrafiltration system and buffer (20 mM NaH.sub.2PO.sub.4, 500 mM NaCl, pH 6.0) exchange was performed to facilitate VLP assembly. The purification results showed that the purification yields of the six C-terminus modified HPV11L1 proteins were all high. It was worth noting that although the expression levels of 11L1CS2 and 11L1CS6 were comparable to that of wild-type 11L1, the purification yield was about 1.5 times that of wild-type 11L1. The above purification methods were all publicly available, for example, the patents CN101293918B, CN1976718A, etc.

The purified wild-type HPV11L1 protein or C-terminus modified HPV11L1 protein solutions were subjected to DLS particle size analysis (Zetasizer Nano ZS 90™ Dynamic Light Scatterer, Malvern), and the results were as shown in Table 2, wherein the DLS analysis plots of wild-type HPV11L1, 11L1CS1, 11LICS3, 11L1CS4 and 11L1CS5 were as shown in FIGS. 2A to 2E.

TABLE 2

DLS analysis of HPV11L1 proteins

| Protein name | Hydraulic diameter (nm) | PDI |
|---|---|---|
| HPV11L1 | 117 | 0.174 |
| 11L1CS1 | 143 | 0.214 |
| 11L1CS2 | 126 | 0.245 |
| 11L1CS3 | 95.2 | 0.175 |
| 11L1CS4 | 121 | 0.184 |
| 11L1CS5 | 119 | 0.218 |
| 11L1CS6 | 137 | 0.149 |

Figure 3A:
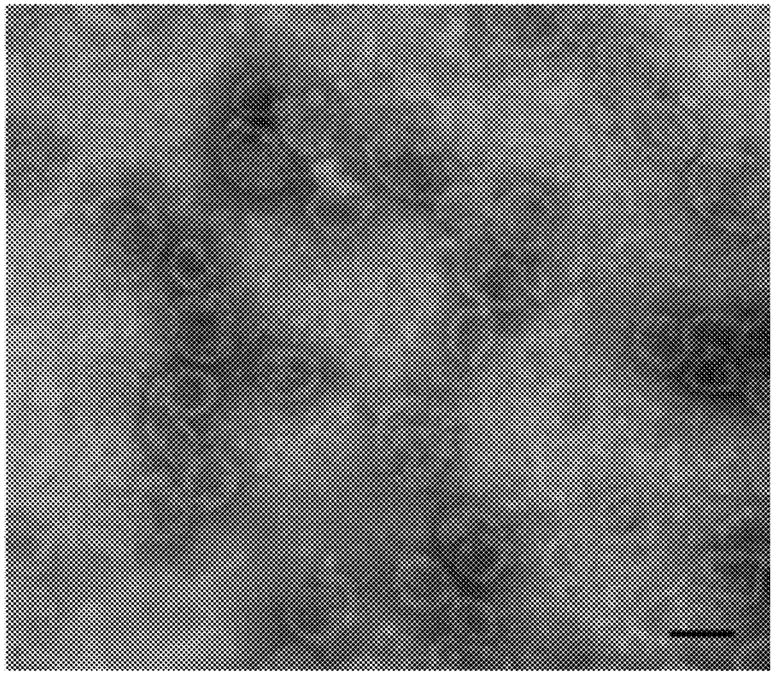
FIGS. 3A to 3C show the transmission electron microscopy observation results of wild-type HPV11L1, 11L1CS4 and 11L1CS5 VLPs obtained after purification in Example 7 of the present application. A large number of virus-like particles with diameters of about 35-55 nm can be seen in the field. The particle size is consistent with the theoretical value and has good uniformity. Bar=50 nm.
Figure 3B:
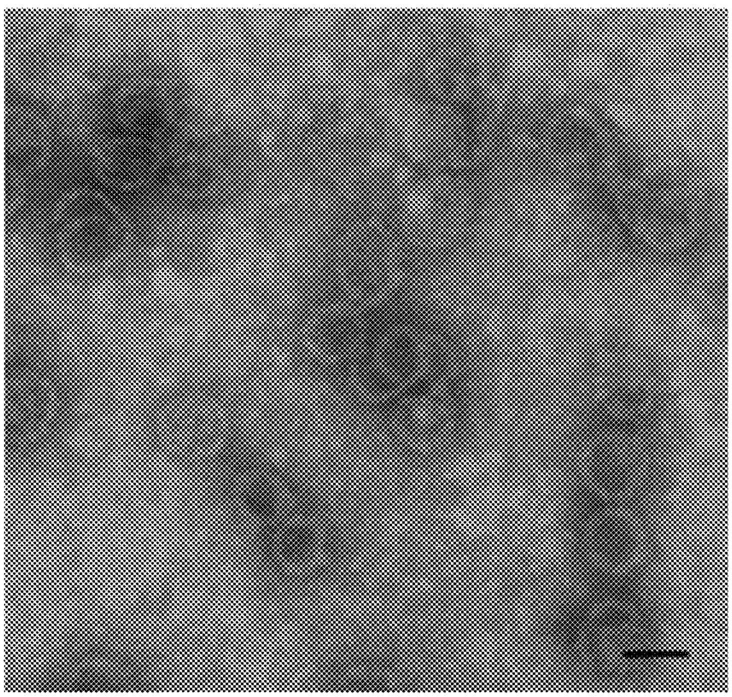
Figure 3C:
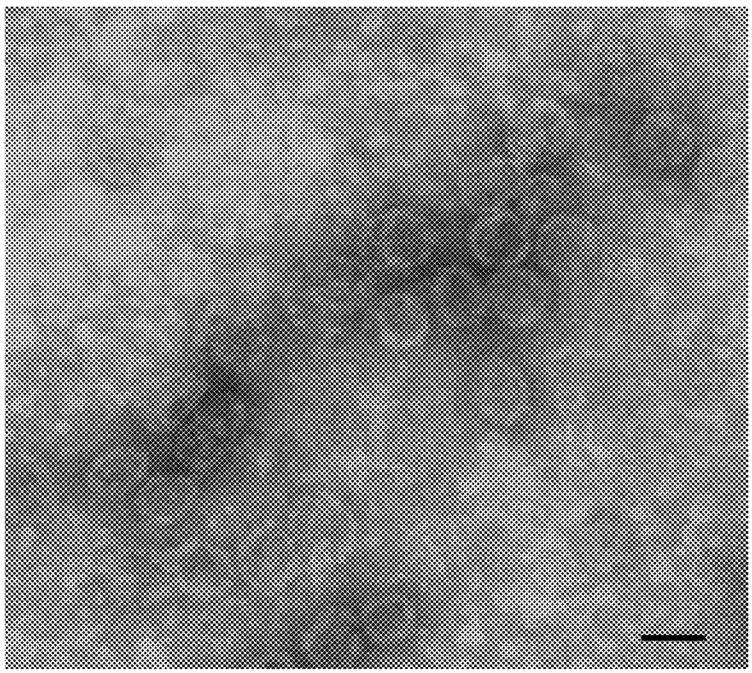

Example 7: Transmission Electron Microscopy Observation of C-Terminus Modified HPV11L1 VLPs The C-terminus modified HPV11L1 VLPs were purified respectively according to the chromatographic purification method described in Example 6. The VLPs after dialysis were prepared on copper mesh, stained with 1% uranium acetate, fully dried and then observed using JEM-1400 electron microscope (Olympus). Some of the results were as shown in FIGS. 3A to 3C. The C-terminus modified HPV11L1 VLPs were approximately 35-55 nm in diameter and had a regular shape. Methods of copper mesh preparation and electron microscopy observation were all publicly available, for example, the patent CN 101148661 B.

Example 8: Immunization of Mice with C-Terminus Modified HPV11L1 VLPs and Determination of Neutralizing Antibody Titers 4-6 weeks old BALB/c mice were randomly divided into groups of 5 mice and immunized with wild-type HPV11L1 VLP and the C-terminus modified HPV11L1 VLPs respectively. L1 VLP was intramuscularly injected at an immunizing dose of 0.1 μg at Week 0 and Week 2 for a total of 2 doses. Tail vein blood was collected 2 weeks after the second immunization and serum was isolated.

Figure 4:
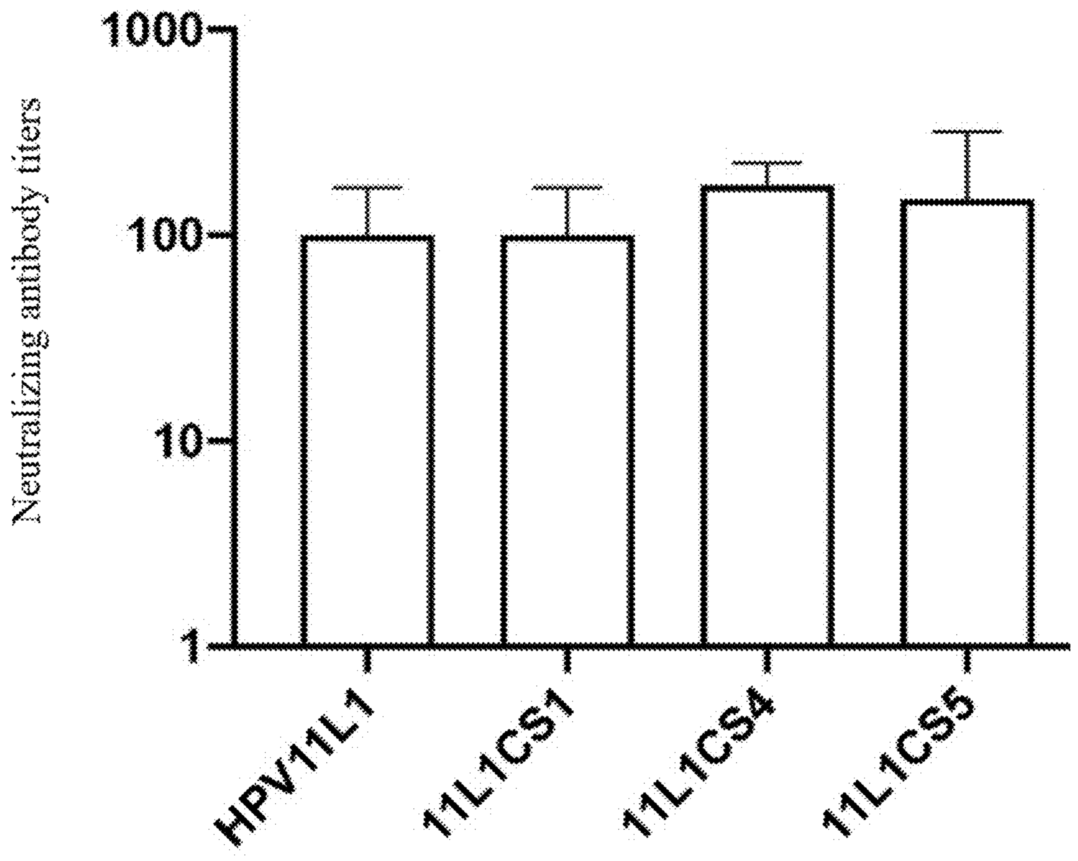
FIG. 4 shows the analysis of HPV11 neutralizing antibody titers in immune serum of mice inoculated with wild-type HPV11L1, 11L1CS1, 11L1CS4 and 11L1CS5 VLPs in Example 8 of the present application.

HPV11 pseudovirus was used to detect HPV11 neutralizing antibody titers in immune serum, and the results were as shown in FIG. 4. Wild-type HPV11L1 VLP, 11L1CS1 VLP, 11L1CS4 VLP and 11L1CS5 VLP were all effective in inducing neutralizing antibodies in immunized mice, and the neutralizing antibody titers induced by the C-terminus modified HPV11L1 VLPs and wild-type HPV11L1 VLP were not significantly different.

The methods of pseudovirus preparation and pseudovirus neutralization experiments were publicly available, for example, the patent CN 104418942A.

In summary, the inventor found that the expression levels of mutants obtained by C-terminus amino acid substitution modification of HPV11LT vary from each other, and are irregular. Therefore, it cannot be expected that HPV11L1 mutants with high expression level, effective assembly and good immune activity can be obtained by the method of C-terminus substitution modification. The HPV11L1 mutants of the present application obtained by C-terminus amino acid substitution modification can be used in the formulation of multivalent HPV prophylactic vaccine and in the construction of broad-spectrum HPV prophylactic vaccine, and has good research and development prospects.

Description of Sequences

```
SEQ ID No. 1: HPV11L1
  1         MWRPSDSTVY VPPPNPVSKV
 21         VATDAYVKRT NIFYHASSSR
 41         LLAVGHPYYS IKKVNKTVVP
 61         KVSGYQYRVF KVVLPDPNKF
 81         ALPDSSLFDP TTQRLVWACT
101         GLEVGRGQPL GVGVSGHPLL
121         NKYDDVENSG GYGGNPGQDN
141         RVNVGMDYKQ TQLCMVGCAP
161         PLGEHWGKGT QCSNTSVQNG
181         DCPPLELITS VIQDGDMVDT
201         GFGAMNFADL QTNKSDVPLD
221         ICGTVCKYPD YLQMAADPYG
241         DRLFFYLRKE QMFARHFFNR
261         AGTVGEPVPD DLLVKGGNNR
281         SSVASSIYVH TPSGSLVSSE
301         AQLFNKPYWL QKAQGHNNGI
321         CWGNHLFVTV VDTTRSTNMT
341         LCASVSKSAT YTNSDYKEYM
361         RHVEEFDLQF IFQLCSITLS
381         AEVMAYIHTM NPSVLEDWNF
401         GLSPPPNGTL EDTYRYVQSQ
421         AITCQKPTPE KEKQDPYKDM
441         SFWEVNLKEK FSSELDQFPL
461         GRKFLLQSGY RGRTSARTGI
481         KRPAVSKPST APKRKRTKTK
501         K

SEQ ID No. 2: 11L1CS1
  1         MWRPSDSTVY VPPPNPVSKV
 21         VATDAYVKRT NIFYHASSSR
 41         LLAVGHPYYS IKKVNKTVVP
 61         KVSGYQYRVF KVVLPDPNKF
 81         ALPDSSLFDP TTQRLVWACT
101         GLEVGRGQPL GVGVSGHPLL
121         NKYDDVENSG GYGGNPGQDN
141         RVNVGMDYKQ TQLCMVGCAP
161         PLGEHWGKGT QCSNTSVQNG
```

-continued

```
181   DCPPLELITS VIQDGDMVDT

201   GFGAMNFADL QTNKSDVPLD

221   ICGTVCKYPD YLQMAADPYG

241   DRLFFYLRKE QMFARHFFNR

261   AGTVGEPVPD DLLVKGGNNR

281   SSVASSIYVH TPSGSLVSSE

301   AQLFNKPYWL QKAQGHNNGI

321   CWGNHLFVTV VDTTRSTNMT

341   LCASVSKSAT YTNSDYKEYM

361   RHVEEFDLQF IFQLCSITLS

381   AEVMAYIHTM NPSVLEDWNF

401   GLSPPPNGTL EDTYRYVQSQ

421   AITCQKPTPE KEKQDPYKDM

441   SFWEVNLKEK FSSELDQFPL

461   GRKFLLQSGY RGGTSARTGI

481   GSPAVSKPST APDGSRTDTK

501   K
```

SEQ ID No. 3: 11L1CS2

```
  1   MWRPSDSTVY VPPPNPVSKV

 21   VATDAYVKRT NIFYHASSSR

 41   LLAVGHPYYS IKKVNKTVVP

 61   KVSGYQYRVF KVVLPDPNKF

 81   ALPDSSLFDP TTQRLVWACT

101   GLEVGRGQPL GVGVSGHPLL

121   NKYDDVENSG GYGGNPGQDN

141   RVNVGMDYKQ TQLCMVGCAP

161   PLGEHWGKGT QCSNTSVQNG

181   DCPPLELITS VIQDGDMVDT

201   GFGAMNFADL QTNKSDVPLD

221   ICGTVCKYPD YLQMAADPYG

241   DRLFFYLRKE QMFARHFFNR

261   AGTVGEPVPD DLLVKGGNNR

281   SSVASSIYVH TPSGSLVSSE

301   AQLFNKPYWL QKAQGHNNGI

321   CWGNHLFVTV VDTTRSTNMT

341   LCASVSKSAT YTNSDYKEYM

361   RHVEEFDLQF IFQLCSITLS

381   AEVMAYIHTM NPSVLEDWNF

401   GLSPPPNGTL EDTYRYVQSQ

421   AITCQKPTPE KEKQDPYKDM

441   SFWEVNLKEK FSSELDQFPL
```

-continued

```
461        GRKFLLQSGY RGGTSARTGI

481        GSPAVSKPST APGDSRTDTK

501        K
```

SEQ ID No. 4: 11L1CS3

```
  1        MWRPSDSTVY VPPPNPVSKV

 21        VATDAYVKRT NIFYHASSSR

 41        LLAVGHPYYS IKKVNKTVVP

 61        KVSGYQYRVF KVVLPDPNKF

 81        ALPDSSLFDP TTQRLVWACT

101        GLEVGRGQPL GVGVSGHPLL

121        NKYDDVENSG GYGGNPGQDN

141        RVNVGMDYKQ TQLCMVGCAP

161        PLGEHWGKGT QCSNTSVQNG

181        DCPPLELITS VIQDGDMVDT

201        GFGAMNFADL QTNKSDVPLD

221        ICGTVCKYPD YLQMAADPYG

241        DRLFFYLRKE QMFARHFFNR

261        AGTVGEPVPD DLLVKGGNNR

281        SSVASSIYVH TPSGSLVSSE

301        AQLFNKPYWL QKAQGHNNGI

321        CWGNHLFVTV VDTTRSTNMT

341        LCASVSKSAT YTNSDYKEYM

361        RHVEEFDLQF IFQLCSITLS

381        AEVMAYIHTM NPSVLEDWNF

401        GLSPPPNGTL EDTYRYVQSQ

421        AITCQKPTPE KEKQDPYKDM

441        SFWEVNLKEK FSSELDQFPL

461        GRKFLLQSGY RGGTSARTGI

481        GSPAVSSPST APSGSGTGTK

501        K
```

SEQ ID No. 5: 11L1CS4

```
  1        MWRPSDSTVY VPPPNPVSKV

 21        VATDAYVKRT NIFYHASSSR

 41        LLAVGHPYYS IKKVNKTVVP

 61        KVSGYQYRVF KVVLPDPNKF

 81        ALPDSSLFDP TTQRLVWACT

101        GLEVGRGQPL GVGVSGHPLL

121        NKYDDVENSG GYGGNPGQDN

141        RVNVGMDYKQ TQLCMVGCAP

161        PLGEHWGKGT QCSNTSVQNG

181        DCPPLELITS VIQDGDMVDT
```

-continued

```
201 GFGAMNFADL QTNKSDVPLD

221 ICGTVCKYPD YLQMAADPYG

241 DRLFFYLRKE QMFARHFFNR

261 AGTVGEPVPD DLLVKGGNNR

281 SSVASSIYVH TPSGSLVSSE

301 AQLFNKPYWL QKAQGHNNGI

321 CWGNHLFVTV VDTTRSTNMT

341 LCASVSKSAT YTNSDYKEYM

361 RHVEEFDLQF IFQLCSITLS

381 AEVMAYIHTM NPSVLEDWNF

401 GLSPPPNGTL EDTYRYVQSQ

421 AITCQKPTPE KEKQDPYKDM

441 SFWEVNLKEK FSSELDQFPL

461 GRKFLLQSGY RGGTSARTGI

481 GSPAVSKPST APSGSGTGTK

501 K
```

SEQ ID No. 6: 11L1CS5

```
  1 MWRPSDSTVY VPPPNPVSKV

 21 VATDAYVKRT NIFYHASSSR

 41 LLAVGHPYYS IKKVNKTVVP

 61 KVSGYQYRVF KVVLPDPNKF

 81 ALPDSSLFDP TTQRLVWACT

101 GLEVGRGQPL GVGVSGHPLL

121 NKYDDVENSG GYGGNPGQDN

141 RVNVGMDYKQ TQLCMVGCAP

161 PLGEHWGKGT QCSNTSVQNG

181 DCPPLELITS VIQDGDMVDT

201 GFGAMNFADL QTNKSDVPLD

221 ICGTVCKYPD YLQMAADPYG

241 DRLFFYLRKE QMFARHFFNR

261 AGTVGEPVPD DLLVKGGNNR

281 SSVASSIYVH TPSGSLVSSE

301 AQLFNKPYWL QKAQGHNNGI

321 CWGNHLFVTV VDTTRSTNMT

341 LCASVSKSAT YTNSDYKEYM

361 RHVEEFDLQF IFQLCSITLS

381 AEVMAYIHTM NPSVLEDWNF

401 GLSPPPNGTL EDTYRYVQSQ

421 AITCQKPTPE KEKQDPYKDM

441 SFWEVNLKEK FSSELDQFPL

461 GRKFLLQSGY RGDTSARTGI
```

-continued

481 GSPAVSKPST APDGSRTDTK

501 K

SEQ ID No. 7: 11L1CS6

1 MWRPSDSTVY VPPPNPVSKV

21 VATDAYVKRT NIFYHASSSR

41 LLAVGHPYYS IKKVNKTVVP

61 KVSGYQYRVF KVVLPDPNKF

81 ALPDSSLFDP TTQRLVWACT

101 GLEVGRGQPL GVGVSGHPLL

121 NKYDDVENSG GYGGNPGQDN

141 RVNVGMDYKQ TQLCMVGCAP

161 PLGEHWGKGT QCSNTSVQNG

181 DCPPLELITS VIQDGDMVDT

201 GFGAMNFADL QTNKSDVPLD

221 ICGTVCKYPD YLQMAADPYG

241 DRLFFYLRKE QMFARHFFNR

261 AGTVGEPVPD DLLVKGGNNR

281 SSVASSIYVH TPSGSLVSSE

301 AQLFNKPYWL QKAQGHNNGI

321 CWGNHLFVTV VDTTRSTNMT

341 LCASVSKSAT YTNSDYKEYM

361 RHVEEFDLQF IFQLCSITLS

381 AEVMAYIHTM NPSVLEDWNF

401 GLSPPPNGTL EDTYRYVQSQ

421 AITCQKPTPE KEKQDPYKDM

441 SFWEVNLKEK FSSELDQFPL

461 GRKFLLQSGY RGGTSARTGI

481 DSPAVSKPST APDGSRTDTK

501 K

SEQ ID No. 8: HPV11L1nt

ATGTGGCGTCCCTCAGATTCAACCGTGTACGTCCCCCCCCCTAATCCCGTGTC

CAAAGTCGTCGCTACCGACGCCTACGTCAAGAGGACAAATATCTTCTACCAC

GCTTCATCCAGCCGCTTGTTGGCCGTCGGCCACCCCTACTACAGCATTAAGAA

GGTCAATAAGACCGTCGTGCCCAAAGTCAGCGGCTACCAGTACCGCGTCTTC

AAAGTGGTCCTCCCCGACCCCAATAAATTCGCCCTGCCCGACAGCTCCCTCT

TCGATCCTACCACCCAAAGGCTGGTGTGGGCCTGTACCGGCCTCGAAGTGGG

TCGCGGCCAGCCCCTGGGTGTCGGCGTCTCCGGCCACCCCCTCTTGAATAAG

TACGACGACGTGGAGAACTCCGGCGGCTACGGCGGCAACCCCGGCCAAGAC

AACCGCGTCAACGTGGGCATGGACTACAAGCAGACACAATTGTGCATGGTCG

GTTGCGCCCCCCCCCTGGGCGAGCACTGGGGCAAAGGCACCCAGTGCAGCA

ACACAAGCGTGCAGAACGGCGATTGTCCTCCCCTCGAGTTGATCACATCCGT

CATCCAAGACGGCGATATGGTCGACACCGGTTTCGGCGCCATGAACTTCGCC

-continued

GATCTGCAGACAAACAAGAGCGACGTCCCTTTGGACATCTGCGGCACCGTGT

GTAAGTACCCCGACTACCTCCAGATGGCCGCCGATCCCTACGGCGACCGCCT

CTTCTTCTACCTCAGGAAAGAGCAGATGTTCGCCCGCCATTTCTTCAACCGCG

CTGGCACCGTCGGCGAGCCCGTCCCCGACGATCTCCTCGTGAAGGGCGGCA

ACAATCGCAGCAGCGTGGCCTCCTCCATCTACGTGCACACCCCCTCCGGTAG

CCTCGTCAGCAGCGAAGCCCAGCTGTTCAACAAGCCCTACTGGTTGCAGAA

AGCCCAAGGCCACAATAACGGCATCTGTTGGGGCAATCATCTCTTCGTCACC

GTCGTGGACACAACCAGGTCCACCAACATGACCTTGTGCGCCAGCGTCAGC

AAGAGCGCCACCTACACCAACAGCGACTACAAAGAGTACATGAGGCACGTC

GAAGAATTCGACCTGCAATTCATCTTCCAGCTCTGCTCAATCACCCTGAGCGC

CGAGGTGATGGCTTACATCCATACCATGAACCCCAGCGTCCTCGAAGATTGG

AATTTCGGTCTGAGCCCCCCCCCCAACGGCACCCTCGAAGACACCTACCGCT

ACGTGCAAAGCCAAGCTATCACATGCCAAAAGCCTACCCCCGAGAAGGAGA

AGCAAGACCCTTACAAAGACATGTCCTTCTGGGAAGTCAATCTGAAGGAGA

AATTCAGCTCCGAGCTGGACCAATTCCCTTTGGGCAGGAAATTCCTGCTCCA

GTCCGGCTACAGGGGCCGAACCAGCGCCAGGACCGGCATCAAAAGGCCCGC

CGTCAGCAAACCTAGCACCGCTCCTAAGAGGAAGAGGACAAAGACAAAGA

AATAA

SEQ ID No. 9: 11L1CS1nt
ATGTGGCGTCCCTCAGATTCAACCGTGTACGTCCCCCCCCCTAATCCCGTGTC

CAAAGTCGTCGCTACCGACGCCTACGTCAAGAGGACAAATATCTTCTACCAC

GCTTCATCCAGCCGCTTGTTGGCCGTCGGCCACCCCTACTACAGCATTAAGAA

GGTCAATAAGACCGTCGTGCCCAAAGTCAGCGGCTACCAGTACCGCGTCTTC

AAAGTGGTCCTCCCCGACCCCAATAAATTCGCCCTGCCCGACAGCTCCCTCT

TCGATCCTACCACCCAAAGGCTGGTGTGGGCCTGTACCGGCCTCGAAGTGGG

TCGCGGCCAGCCCCTGGGTGTCGGCGTCTCCGGCCACCCCCTCTTGAATAAG

TACGACGACGTGGAGAACTCCGGCGGCTACGGCGGCAACCCCGGCCAAGAC

AACCGCGTCAACGTGGGCATGGACTACAAGCAGACACAATTGTGCATGGTCG

GTTGCGCCCCCCCCCTGGGCGAGCACTGGGGCAAAGGCACCCAGTGCAGCA

ACACAAGCGTGCAGAACGGCGATTGTCCTCCCCTCGAGTTGATCACATCCGT

CATCCAAGACGGCGATATGGTCGACACCGGTTTCGGCGCCATGAACTTCGCC

GATCTGCAGACAAACAAGAGCGACGTCCCTTTGGACATCTGCGGCACCGTGT

GTAAGTACCCCGACTACCTCCAGATGGCCGCCGATCCCTACGGCGACCGCCT

CTTCTTCTACCTCAGGAAAGAGCAGATGTTCGCCCGCCATTTCTTCAACCGCG

CTGGCACCGTCGGCGAGCCCGTCCCCGACGATCTCCTCGTGAAGGGCGGCA

ACAATCGCAGCAGCGTGGCCTCCTCCATCTACGTGCACACCCCCTCCGGTAG

CCTCGTCAGCAGCGAAGCCCAGCTGTTCAACAAGCCCTACTGGTTGCAGAA

AGCCCAAGGCCACAATAACGGCATCTGTTGGGGCAATCATCTCTTCGTCACC

GTCGTGGACACAACCAGGTCCACCAACATGACCTTGTGCGCCAGCGTCAGC

AAGAGCGCCACCTACACCAACAGCGACTACAAAGAGTACATGAGGCACGTC

GAAGAATTCGACCTGCAATTCATCTTCCAGCTCTGCTCAATCACCCTGAGCGC

-continued

CGAGGTGATGGCTTACATCCATACCATGAACCCCAGCGTCCTCGAAGATTGG

AATTTCGGTCTGAGCCCCCCCCCCAACGGCACCCTCGAAGACACCTACCGCT

ACGTGCAAAGCCAAGCTATCACATGCCAAAAGCCTACCCCCGAGAAGGAGA

AGCAAGACCCTTACAAAGACATGTCCTTCTGGGAAGTCAATCTGAAGGAGA

AATTCAGCTCCGAGCTGGACCAATTCCCTTTGGGCAGGAAATTCCTGCTCCA

GTCCGGCTAC AGG GGC GGA ACC AGC GCC AGG ACC GGC ATC GGA AGT

CCC GCC GTC AGC AAA CCT AGC ACC GCT CCT GAC GGA AGC AGG ACA

GAC ACA AAG AAA TAA

SEQ ID No. 10: 11L1CS2nt
ATGTGGCGTCCCTCAGATTCAACCGTGTACGTCCCCCCCCCTAATCCCGTGTC

CAAAGTCGTCGCTACCGACGCCTACGTCAAGAGGACAAATATCTTCTACCAC

GCTTCATCCAGCCGCTTGTTGGCCGTCGGCCACCCCTACTACAGCATTAAGAA

GGTCAATAAGACCGTCGTGCCCAAAGTCAGCGGCTACCAGTACCGCGTCTTC

AAAGTGGTCCTCCCCGACCCCAATAAATTCGCCCTGCCCGACAGCTCCCTCT

TCGATCCTACCACCCAAAGGCTGGTGTGGGCCTGTACCGGCCTCGAAGTGGG

TCGCGGCCAGCCCCTGGGTGTCGGCGTCTCCGGCCACCCCCTCTTGAATAAG

TACGACGACGTGGAGAACTCCGGCGGCTACGGCGGCAACCCCGGCCAAGAC

AACCGCGTCAACGTGGGCATGGACTACAAGCAGACACAATTGTGCATGGTCG

GTTGCGCCCCCCCCCTGGGCGAGCACTGGGGCAAAGGCACCCAGTGCAGCA

ACACAAGCGTGCAGAACGGCGATTGTCCTCCCCTCGAGTTGATCACATCCGT

CATCCAAGACGGCGATATGGTCGACACCGGTTTCGGCGCCATGAACTTCGCC

GATCTGCAGACAAACAAGAGCGACGTCCCTTTGGACATCTGCGGCACCGTGT

GTAAGTACCCCGACTACCTCCAGATGGCCGCCGATCCCTACGGCGACCGCCT

CTTCTTCTACCTCAGGAAAGAGCAGATGTTCGCCCGCCATTTCTTCAACCGCG

CTGGCACCGTCGGCGAGCCCGTCCCCGACGATCTCCTCGTGAAGGGCGGCA

ACAATCGCAGCAGCGTGGCCTCCTCCATCTACGTGCACACCCCCTCCGGTAG

CCTCGTCAGCAGCGAAGCCCAGCTGTTCAACAAGCCCTACTGGTTGCAGAA

AGCCCAAGGCCACAATAACGGCATCTGTTGGGGCAATCATCTCTTCGTCACC

GTCGTGGACACAACCAGGTCCACCAACATGACCTTGTGCGCCAGCGTCAGC

AAGAGCGCCACCTACACCAACAGCGACTACAAAGAGTACATGAGGCACGTC

GAAGAATTCGACCTGCAATTCATCTTCCAGCTCTGCTCAATCACCCTGAGCGC

CGAGGTGATGGCTTACATCCATACCATGAACCCCAGCGTCCTCGAAGATTGG

AATTTCGGTCTGAGCCCCCCCCCCAACGGCACCCTCGAAGACACCTACCGCT

ACGTGCAAAGCCAAGCTATCACATGCCAAAAGCCTACCCCCGAGAAGGAGA

AGCAAGACCCTTACAAAGACATGTCCTTCTGGGAAGTCAATCTGAAGGAGA

AATTCAGCTCCGAGCTGGACCAATTCCCTTTGGGCAGGAAATTCCTGCTCCA

GTCCGGCTAC AGG GGC GGA ACC AGC GCC AGG ACC GGC ATC GGA AGT

CCC GCC GTC AGC AAA CCT AGC ACC GCT CCT GGA GAC AGC AGG ACA

GAC ACA AAG AAA TAA

-continued

SEQ ID No. 11: 11L1CS3nt
ATGTGGCGTCCCTCAGATTCAACCGTGTACGTCCCCCCCCCTAATCCCGTGTC

CAAAGTCGTCGCTACCGACGCCTACGTCAAGAGGACAAATATCTTCTACCAC

GCTTCATCCAGCCGCTTGTTGGCCGTCGGCCACCCCTACTACAGCATTAAGAA

GGTCAATAAGACCGTCGTGCCCAAAGTCAGCGGCTACCAGTACCGCGTCTTC

AAAGTGGTCCTCCCCGACCCCAATAAATTCGCCCTGCCCGACAGCTCCCTCT

TCGATCCTACCACCCAAAGGCTGGTGTGGGCCTGTACCGGCCTCGAAGTGGG

TCGCGGCCAGCCCCTGGGTGTCGGCGTCTCCGGCCACCCCCTCTTGAATAAG

TACGACGACGTGGAGAACTCCGGCGGCTACGGCGGCAACCCCGGCCAAGAC

AACCGCGTCAACGTGGGCATGGACTACAAGCAGACACAATTGTGCATGGTCG

GTTGCGCCCCCCCCCTGGGCGAGCACTGGGGCAAAGGCACCCAGTGCAGCA

ACACAAGCGTGCAGAACGGCGATTGTCCTCCCCTCGAGTTGATCACATCCGT

CATCCAAGACGGCGATATGGTCGACACCGGTTTCGGCGCCATGAACTTCGCC

GATCTGCAGACAAACAAGAGCGACGTCCCTTTGGACATCTGCGGCACCGTGT

GTAAGTACCCCGACTACCTCCAGATGGCCGCCGATCCCTACGGCGACCGCCT

CTTCTTCTACCTCAGGAAAGAGCAGATGTTCGCCCGCCATTTCTTCAACCGCG

CTGGCACCGTCGGCGAGCCCGTCCCCGACGATCTCCTCGTGAAGGGCGGCA

ACAATCGCAGCAGCGTGGCCTCCTCCATCTACGTGCACACCCCCTCCGGTAG

CCTCGTCAGCAGCGAAGCCCAGCTGTTCAACAAGCCCTACTGGTTGCAGAA

AGCCCAAGGCCACAATAACGGCATCTGTTGGGGCAATCATCTCTTCGTCACC

GTCGTGGACACAACCAGGTCCACCAACATGACCTTGTGCGCCAGCGTCAGC

AAGAGCGCCACCTACACCAACAGCGACTACAAAGAGTACATGAGGCACGTC

GAAGAATTCGACCTGCAATTCATCTTCCAGCTCTGCTCAATCACCCTGAGCGC

CGAGGTGATGGCTTACATCCATACCATGAACCCCAGCGTCCTCGAAGATTGG

AATTTCGGTCTGAGCCCCCCCCCCAACGGCACCCTCGAAGACACCTACCGCT

ACGTGCAAAGCCAAGCTATCACATGCCAAAAGCCTACCCCCGAGAAGGAGA

AGCAAGACCCTTACAAAGACATGTCCTTCTGGGAAGTCAATCTGAAGGAGA

AATTCAGCTCCGAGCTGGACCAATTCCCTTTGGGCAGGAAATTCCTGCTCCA

GTCCGGCTAC AGG GGC GGA ACC AGC GCC AGG ACC GGC ATC GGA AGT

CCC GCC GTC AGC TCA CCT AGC ACC GCT CCT AGC GGA AGC GGc ACA GGC

ACA AAG AAA TAA

SEQ ID No. 12: 11L1CS4nt
ATGTGGCGTCCCTCAGATTCAACCGTGTACGTCCCCCCCCCTAATCCCGTGTC

CAAAGTCGTCGCTACCGACGCCTACGTCAAGAGGACAAATATCTTCTACCAC

GCTTCATCCAGCCGCTTGTTGGCCGTCGGCCACCCCTACTACAGCATTAAGAA

GGTCAATAAGACCGTCGTGCCCAAAGTCAGCGGCTACCAGTACCGCGTCTTC

AAAGTGGTCCTCCCCGACCCCAATAAATTCGCCCTGCCCGACAGCTCCCTCT

TCGATCCTACCACCCAAAGGCTGGTGTGGGCCTGTACCGGCCTCGAAGTGGG

TCGCGGCCAGCCCCTGGGTGTCGGCGTCTCCGGCCACCCCCTCTTGAATAAG

TACGACGACGTGGAGAACTCCGGCGGCTACGGCGGCAACCCCGGCCAAGAC

AACCGCGTCAACGTGGGCATGGACTACAAGCAGACACAATTGTGCATGGTCG

-continued

GTTGCGCCCCCCCCCTGGGCGAGCACTGGGGCAAAGGCACCCAGTGCAGCA

ACACAAGCGTGCAGAACGGCGATTGTCCTCCCCTCGAGTTGATCACATCCGT

CATCCAAGACGGCGATATGGTCGACACCGGTTTCGGCGCCATGAACTTCGCC

GATCTGCAGACAAACAAGAGCGACGTCCCTTTGGACATCTGCGGCACCGTGT

GTAAGTACCCCGACTACCTCCAGATGGCCGCCGATCCCTACGGCGACCGCCT

CTTCTTCTACCTCAGGAAAGAGCAGATGTTCGCCCGCCATTTCTTCAACCGCG

CTGGCACCGTCGGCGAGCCCGTCCCCGACGATCTCCTCGTGAAGGGCGGCA

ACAATCGCAGCAGCGTGGCCTCCTCCATCTACGTGCACACCCCCTCCGGTAG

CCTCGTCAGCAGCGAAGCCCAGCTGTTCAACAAGCCCTACTGGTTGCAGAA

AGCCCAAGGCCACAATAACGGCATCTGTTGGGGCAATCATCTCTTCGTCACC

GTCGTGGACACAACCAGGTCCACCAACATGACCTTGTGCGCCAGCGTCAGC

AAGAGCGCCACCTACACCAACAGCGACTACAAAGAGTACATGAGGCACGTC

GAAGAATTCGACCTGCAATTCATCTTCCAGCTCTGCTCAATCACCCTGAGCGC

CGAGGTGATGGCTTACATCCATACCATGAACCCCAGCGTCCTCGAAGATTGG

AATTTCGGTCTGAGCCCCCCCCCCAACGGCACCCTCGAAGACACCTACCGCT

ACGTGCAAAGCCAAGCTATCACATGCCAAAAGCCTACCCCCGAGAAGGAGA

AGCAAGACCCTTACAAAGACATGTCCTTCTGGGAAGTCAATCTGAAGGAGA

AATTCAGCTCCGAGCTGGACCAATTCCCTTTGGGCAGGAAATTCCTGCTCCA

GTCCGGCTAC AGG GGC GGA ACC AGC GCC AGG ACC GGC ATC GGA AGT

CCC GCC GTC AGC AAA CCT AGC ACC GCT CCT AGC GGA AGC GGC ACA GGC

ACA AAG AAA TAA

SEQ ID No. 13: 11L1CS5nt

ATGTGGCGTCCCTCAGATTCAACCGTGTACGTCCCCCCCCCTAATCCCGTGTC

CAAAGTCGTCGCTACCGACGCCTACGTCAAGAGGACAAATATCTTCTACCAC

GCTTCATCCAGCCGCTTGTTGGCCGTCGGCCACCCCTACTACAGCATTAAGAA

GGTCAATAAGACCGTCGTGCCCAAAGTCAGCGGCTACCAGTACCGCGTCTTC

AAAGTGGTCCTCCCCGACCCCAATAAATTCGCCCTGCCCGACAGCTCCCTCT

TCGATCCTACCACCCAAAGGCTGGTGTGGGCCTGTACCGGCCTCGAAGTGGG

TCGCGGCCAGCCCCTGGGTGTCGGCGTCTCCGGCCACCCCCTCTTGAATAAG

TACGACGACGTGGAGAACTCCGGCGGCTACGGCGGCAACCCCGGCCAAGAC

AACCGCGTCAACGTGGGCATGGACTACAAGCAGACACAATTGTGCATGGTCG

GTTGCGCCCCCCCCCTGGGCGAGCACTGGGGCAAAGGCACCCAGTGCAGCA

ACACAAGCGTGCAGAACGGCGATTGTCCTCCCCTCGAGTTGATCACATCCGT

CATCCAAGACGGCGATATGGTCGACACCGGTTTCGGCGCCATGAACTTCGCC

GATCTGCAGACAAACAAGAGCGACGTCCCTTTGGACATCTGCGGCACCGTGT

GTAAGTACCCCGACTACCTCCAGATGGCCGCCGATCCCTACGGCGACCGCCT

CTTCTTCTACCTCAGGAAAGAGCAGATGTTCGCCCGCCATTTCTTCAACCGCG

CTGGCACCGTCGGCGAGCCCGTCCCCGACGATCTCCTCGTGAAGGGCGGCA

ACAATCGCAGCAGCGTGGCCTCCTCCATCTACGTGCACACCCCCTCCGGTAG

CCTCGTCAGCAGCGAAGCCCAGCTGTTCAACAAGCCCTACTGGTTGCAGAA

AGCCCAAGGCCACAATAACGGCATCTGTTGGGGCAATCATCTCTTCGTCACC

-continued

GTCGTGGACACAACCAGGTCCACCAACATGACCTTGTGCGCCAGCGTCAGC

AAGAGCGCCACCTACACCAACAGCGACTACAAAGAGTACATGAGGCACGTC

GAAGAATTCGACCTGCAATTCATCTTCCAGCTCTGCTCAATCACCCTGAGCGC

CGAGGTGATGGCTTACATCCATACCATGAACCCCAGCGTCCTCGAAGATTGG

AATTTCGGTCTGAGCCCCCCCCCCAACGGCACCCTCGAAGACACCTACCGCT

ACGTGCAAAGCCAAGCTATCACATGCCAAAAGCCTACCCCCGAGAAGGAGA

AGCAAGACCCTTACAAAGACATGTCCTTCTGGGAAGTCAATCTGAAGGAGA

AATTCAGCTCCGAGCTGGACCAATTCCCTTTGGGCAGGAAATTCCTGCTCCA

GTCCGGCTAC AGG GGC GAC ACC AGC GCC AGG ACC GGC ATC GGA AGT

CCC GCC GTC AGC AAA CCT AGC ACC GCT CCT GAC GGA AGC AGG ACA

GAC ACA AAG AAA TAA

SEQ ID No. 14: 11L1CS6nt
ATGTGGCGTCCCTCAGATTCAACCGTGTACGTCCCCCCCCCTAATCCCGTGTC

CAAAGTCGTCGCTACCGACGCCTACGTCAAGAGGACAAATATCTTCTACCAC

GCTTCATCCAGCCGCTTGTTGGCCGTCGGCCACCCCTACTACAGCATTAAGAA

GGTCAATAAGACCGTCGTGCCCAAAGTCAGCGGCTACCAGTACCGCGTCTTC

AAAGTGGTCCTCCCCGACCCCAATAAATTCGCCCTGCCCGACAGCTCCCTCT

TCGATCCTACCACCCAAAGGCTGGTGTGGGCCTGTACCGGCCTCGAAGTGGG

TCGCGGCCAGCCCCTGGGTGTCGGCGTCTCCGGCCACCCCCTCTTGAATAAG

TACGACGACGTGGAGAACTCCGGCGGCTACGGCGGCAACCCCGGCCAAGAC

AACCGCGTCAACGTGGGCATGGACTACAAGCAGACACAATTGTGCATGGTCG

GTTGCGCCCCCCCCCTGGGCGAGCACTGGGGCAAAGGCACCCAGTGCAGCA

ACACAAGCGTGCAGAACGGCGATTGTCCTCCCCTCGAGTTGATCACATCCGT

CATCCAAGACGGCGATATGGTCGACACCGGTTTCGGCGCCATGAACTTCGCC

GATCTGCAGACAAACAAGAGCGACGTCCCTTTGGACATCTGCGGCACCGTGT

GTAAGTACCCCGACTACCTCCAGATGGCCGCCGATCCCTACGGCGACCGCCT

CTTCTTCTACCTCAGGAAAGAGCAGATGTTCGCCCGCCATTTCTTCAACCGCG

CTGGCACCGTCGGCGAGCCCGTCCCCGACGATCTCCTCGTGAAGGGCGGCA

ACAATCGCAGCAGCGTGGCCTCCTCCATCTACGTGCACACCCCCTCCGGTAG

CCTCGTCAGCAGCGAAGCCCAGCTGTTCAACAAGCCCTACTGGTTGCAGAA

AGCCCAAGGCCACAATAACGGCATCTGTTGGGGCAATCATCTCTTCGTCACC

GTCGTGGACACAACCAGGTCCACCAACATGACCTTGTGCGCCAGCGTCAGC

AAGAGCGCCACCTACACCAACAGCGACTACAAAGAGTACATGAGGCACGTC

GAAGAATTCGACCTGCAATTCATCTTCCAGCTCTGCTCAATCACCCTGAGCGC

CGAGGTGATGGCTTACATCCATACCATGAACCCCAGCGTCCTCGAAGATTGG

AATTTCGGTCTGAGCCCCCCCCCCAACGGCACCCTCGAAGACACCTACCGCT

ACGTGCAAAGCCAAGCTATCACATGCCAAAAGCCTACCCCCGAGAAGGAGA

AGCAAGACCCTTACAAAGACATGTCCTTCTGGGAAGTCAATCTGAAGGAGA

AATTCAGCTCCGAGCTGGACCAATTCCCTTTGGGCAGGAAATTCCTGCTCCA

-continued

GTCCGGCTAC AGG GGC GGA ACC AGC GCC AGG ACC GGC ATC GAC AGT

CCC GCC GTC AGC AAA CCT AGC ACC GCT CCT GAC GGA AGC AGG ACA

GAC ACA AAG AAA TAA.

What claimed is:

1. A C-terminus modified HPV11 L1 protein having an amino acid sequence selected from the group consisting of: SEQ ID No. 2, SEQ ID No. 3, SEQ ID No. 4, SEQ ID No. 5, SEQ ID No. 6 and SEQ ID No. 7.

2. A polynucleotide encoding a C-terminus modified HPV11 L1 protein comprising an amino acid sequence selected from the group consisting of: SEQ ID No. 2, SEQ ID No. 3, SEQ ID No. 4, SEQ ID No. 5, SEQ ID No. 6 and SEQ ID No. 7.

3. The polynucleotide according to claim 2, wherein the sequence of the polynucleotide is whole-gene optimized using insect cell codons.

4. The polynucleotide according to claim 2, which is as shown in the sequence selected from the group consisting of: SEQ ID No. 9, SEQ ID No. 10, SEQ ID No. 11, SEQ ID No. 12, SEQ ID No. 13 and SEQ ID No. 14.

5. A vector comprising the polynucleotide according to claim 2.

6. The vector according to claim 5, wherein the vector is selected from the group consisting of: a plasmid, a recombinant Bacmid and are combinant baculovirus.

7. A host cell comprising the vector according to claim 5, wherein the host cell is selected from the group consisting of: *E. coli*, yeast cell, and insect cell.

8. A multimer wherein:

the multimer is a pentamer or a virus-like particle; and the multimer comprises or is formed by the C-terminus modified HPV11 L1 protein according to claim 1.

9. A vaccine for preventing a papillomavirus infection, the vaccine comprises: the multimer according to claim 8; an adjuvant; and an excipient or vaccine carrier.

10. The vaccine according to claim 9, wherein the adjuvant is suitable humans.

11. The vaccine according to claim 9, further comprising mucosa-tropic HPV virus-like particle or chimeric virus-like particle; skin-tropic HPV virus-like particle or chimeric virus-like particle; or combinations thereof.

* * * * *